United States Patent
Rii et al.

(10) Patent No.: US 9,801,929 B2
(45) Date of Patent: *Oct. 31, 2017

(54) IMMUNE TOLERANCE INDUCER

(75) Inventors: Ko Rii, Chofu (JP); Kazuo Sakurai, Himeji (JP); Masakazu Kobayashi, Kawanishi (JP); Hironori Ando, Nishitokyo (JP); Sadaharu Higuchi, Nishitokyo (JP); Shiro Takahara, Ikeda (JP)

(73) Assignee: Napajen Pharma, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/237,763

(22) PCT Filed: Jul. 13, 2012

(86) PCT No.: PCT/JP2012/067950
§ 371 (c)(1),
(2), (4) Date: May 2, 2014

(87) PCT Pub. No.: WO2013/021784
PCT Pub. Date: Feb. 14, 2013

(65) Prior Publication Data
US 2014/0294869 A1    Oct. 2, 2014

(30) Foreign Application Priority Data

Aug. 10, 2011  (WO) .................. PCT/JP2011/068265
Feb. 15, 2012  (WO) .................. PCT/JP2012/053583

(51) Int. Cl.
*A61K 31/70* (2006.01)
*C07H 21/02* (2006.01)
(Continued)

(52) U.S. Cl.
CPC ...... *A61K 39/0013* (2013.01); *A61K 31/7105* (2013.01); *A61K 31/716* (2013.01);
(Continued)

(58) Field of Classification Search
USPC .......................................... 514/44; 536/24.5
See application file for complete search history.

(56) References Cited

U.S. PATENT DOCUMENTS 6,106,834 A   8/2000  Lazarovits et al.
8,017,742 B2  9/2011  Sakurai et al.
(Continued)

FOREIGN PATENT DOCUMENTS

EP   2 226 384 A1        9/2010
WO   WO 2007/058323 A1   5/2007
WO   WO 2009/078470 A1   6/2009

OTHER PUBLICATIONS

Suzuki et al. Allergy (2009) vol. 64:387-397.*
(Continued)

*Primary Examiner* — Terra C Gibbs
(74) *Attorney, Agent, or Firm* — Fay Sharpe LLP

(57) ABSTRACT

An object of the present invention is to provide a drug and a method for effectively inducing donor-specific immune tolerance in a recipient in transplantation therapy. A complex of an siRNA for a costimulatory factor and schizophyllan is delivered to a Dectin-1 expressing cell which specifically recognizes schizophyllan to regulate the function of the Dectin-1 expressing cell, and therefore can induce immunosuppression effect as well as induce immune tolerance effectively.

5 Claims, 11 Drawing Sheets

(51) Int. Cl.
  C07H 21/04    (2006.01)
  A61K 39/00    (2006.01)
  A61K 31/7105  (2006.01)
  A61K 31/716   (2006.01)
  C12N 15/11    (2006.01)
  C12N 15/113   (2010.01)
  C12N 5/00     (2006.01)

(52) U.S. Cl.
  CPC .......... *C12N 15/111* (2013.01); *C12N 15/113* (2013.01); *C12N 15/1138* (2013.01); *A61K 2039/57* (2013.01); *C12N 2310/315* (2013.01); *C12N 2320/32* (2013.01); *C12N 2320/50* (2013.01)

(56) References Cited

U.S. PATENT DOCUMENTS

2005/0281815 A1*  12/2005  Eshel ............... C07K 14/70578 424/144.1
2006/0216343 A1    9/2006  Panzer et al.
2007/0009517 A1*   1/2007  De Boer ............... A61K 31/00 424/144.1
2011/0111501 A1*   5/2011  Kubo et al. ................... 435/375

OTHER PUBLICATIONS

Mizu, et al., "Enhancement of the Antisense Effect of Polysaccharide-Polynucleotide Complexes by Preventing the Antisense Oligonucleotide from Binding to the Proteins in the Culture Medium", Bull. Chem. Soc. Japan., vol. 77, pp. 1101-1110 (2004).
Karimi, et al., "Comparison of three techniques for generation of tolerogenic dendritic cells: siRNA, oligonucleotide antisense, and antibody blocking," Hybridoma, vol. 29, No. 6, pp. 473-480 (2010).
Huang, L. et al., "Effect of silencing CD86 expression on antigen presenting cells by siRNA on activation of T lymphocytes," Zhongguo Mianyixue Zazhi, vol. 27, No. 8, pp. 681-685, 695 (2011) (English Abstract only).
Brenner, et al., "Anti-CD40 ligand monoclonal antibody induces a permissive state, but not tolerance, for murine peripheral nerve allografts," Exp. Neurol. 186 (1); pp. 59-69 (2004).
Haanstra, et al., "Prevention of kidney allograph rejection using anti-CD40 and anti CD86 in primates," Transplantation Mar. 2003; 75 (5), pp. 637-643 (2003) (English Abstract only).
Suzuki, et al., "Regulation of allergic response by short interfering RNA," Journal of Japan Society of Immunology & Allergology in Otolaryngology, vol. 28, No. 3, pp. 223-228 (2010). (English Abstract only).
Matsumoto, et al., "Chemically modified polysaccharide schizophyllan for antisense oligonucleotides delivery to enhance the cellular uptake efficiency," Biochimica et Biophysica Acta, vol. 1670, No. 2, pp. 91-104 (2004).
Karinaga, et al., "Galactose-PEG dual conjugation of β-(1→3)-D-glucan schizophyllan for antisense oligonucleotides delivery to enhance the cellular uptake," Biomaterials, vol. 27, No. 8, pp. 1626-1635 (2006).
Karinaga, et al., "PEG-appended β-(1→3)-D-glucan schizophyllan to deliver antisense oligonucleotides with avoiding lysosomal degradation," Biomaterials, vol. 26, No. 23, pp. 4866-4873 (2005).
Mizu, et al., "Antisense oligonucleotides bound in the polysaccharide complex and the enhanced antisense effect due to the low hydrolysis," Biomaterials, vol. 25, No. 15, pp. 3117-3123 (2004).
Mochizuki, et al., "Development of nucleic acid delivery system for targeting antigen presenting cells," Polymer Preprints—58th SPSJ Annual Meeting, vol. 58, No. 2, pp. 5018-5019 (2009).
Mochizuki, et al., "A Novel Polysaccharide/Polynucleotide Complex and its Application to Bio-functional DNA Delivery System," Polymer Journal, vol. 41, No. 5, pp. 343-353 (2009).
Suzuki, et al., "A novel allergen-specific therapy for allergy using CD40-silenced dendritic cells," Journal of Allegy and Clinical Immunology, vol. 125, No. 3, pp. 737-743 (2010).
Torras, et al., "Pre-Transplant Intra-Graft Silencing of CD40 Switches the Rejection Pattern from Humorol to Cellular and Induces Accommodation of the Graft," American Journal of Transplantation, vol. 10, Poster Session III, Abstract #1326, p. 419 (2010).
Karimi, et al., "Effect of CD40 silenced dendritic cells by RNA interference on mice skin allograft rejection," Immunotherapy, vol. 7(2), pp. 111-118 (2015).
Zhang, et al., "Permanent acceptance of mouse cardiac allografts with CD40 siRNA to induce regulatory myeloid cells by use of a novel polysaccharide siRNA delivery system," Gene Therapy, pp. 1-10 (2015).

* cited by examiner

HEK239T Cell

Optical Field    Fluorescence    Merge dHEK Cell

Optical Field    Fluorescence    Merge

A

B

IMMUNE TOLERANCE INDUCER

This application claims priority to and the benefit of PCT International Application Number PCT/JP2012/067950, filed on Jul. 13, 2012, PCT/JP2012/053583, filed on Feb. 15, 2012, and PCT/JP2011/068265, filed Aug. 10, 2011, the disclosures of which are incorporated herein by reference in their entireties.

BACKGROUND

The present invention relates to an immunological tolerance-inducing agent containing a nucleic acid-polysaccharide complex of an siRNA for a costimulatory factor and schizophyllan. Also, the present invention relates to a method for inducing immune tolerance by inhibiting gene expression of a costimulatory factor using the nucleic acid-polysaccharide complex to control the function of Dectin-1 expressing cell such as a dendritic cell, and to a medicine for use in the method. Especially, the present invention relates to a medicine containing a nucleic acid-polysaccharide complex of an siRNA for a costimulatory factor and schizophyllan, which inhibits rejection occurring in organ transplantation and induces immune tolerance.

RNA interference (RNAi) discovered in 1998 has markedly superior efficacy and persistence to conventional antisense methods and is a breakthrough gene expression inhibitory method, and therefore there has been a hope for its pharmaceutical applications. However, a double strand RNA (i.e., siRNA) that shows an RNAi activity is often decomposed during the process from administration to uptake into a target cell or decomposed in a cell, and it has been difficult to form a RISC complex, i.e., its active substance, in a cell. Accordingly, even though it is a superior gene expression inhibitory method, a sufficient effect is not obtainable, and therefore a pharmaceutical product that uses an siRNA is not yet available.

Unmodified siRNAs are decomposed by nuclease that is present in, for example, blood, and few unmodified siRNAs demonstrate an RNAi effect in a target cell. Accordingly, various chemical modifications to give nuclease resistance have been performed on siRNAs. Nevertheless, a high dosage is necessary for effective introduction into a cell. Also, it is known that because administration of a double strand nucleotide into a living body in a high dosage enhances a natural immunoreaction, an unintended effect, i.e., immunostimulatory reaction, appears. Accordingly, a delivery technique to specifically introduce an siRNA into a target cell is necessary. For siRNA delivery techniques, techniques to embed an siRNA, such as liposomes and macromolecular nanomicelles, have been developed. However, in terms of target tropism, these delivery techniques are still within the meaning of passive targeting, and in order to overcome this shortcoming, a procedure for imparting, for example, a molecule that binds to the target cell to an siRNA drug is needed.

With such conventional art as background, a demand exists for positive targeting and a delivery technique for an siRNA that shows an RNAi activity significantly within the target cell. Accordingly, as a delivery method of an siRNA to a dendritic cell, a complex of schizophyllan and a polydeoxyadenine-added siRNA has been proposed (see WO 2009/078470).

Meanwhile, transplantation therapy, in which a donor cell, tissue or organ is transplanted to a patient with organ failure, hematological malignancy or the like, has been established and become a crucial therapy in clinical practice. In transplantation therapy, however, technical improvement for inhibiting donor-specific immunoreaction in a recipient is still demanded. Previously, to prolong the transplanted organ survival in organ transplantation, attempts to block CD40-CD40L pathway or CD28-B7 pathway by various antibodies have been made, but no technique that is capable of effective induction of donor-specific tolerance and put into practical use has been found (See Exp Neurol. 2004 March; 186(1): 59-69; Transplantation 2003; 75(5): 637-643).

SUMMARY OF INVENTION

A primary object of the present invention is to provide a medicine and a method for effectively inducing donor-specific immune tolerance in a recipient in transplantation therapy.

Having carried out diligent research to solve the foregoing problems, the inventors found that, surprisingly, a complex of an siRNA for a costimulatory factor and schizophyllan can be delivered to Dectin-1 expressing cell which specifically recognizes schizophyllan to regulate the function of the Dectin-1 expressing cell, and therefore can induce immunosuppressing effect as well as immune tolerance effectively. Actually, the inventors found that in a cardiac transplantation model using a complex of an siRNA for CD40 and schizophyllan, the complex exhibits a highly excellent immune tolerance effect. Based on these findings, the inventors carried out further research and arrived at the present invention.

The present invention provides, for example, an immunological tolerance-inducing agent and a method for inducing immune tolerance as follows:

An immunological tolerance-inducing agent used for inducing donor-specific immune tolerance in a recipient in transplantation therapy of a donor cell, tissue or organ, containing a nucleic acid-polysaccharide complex of an siRNA for a costimulatory factor and schizophyllan.

The above immunological tolerance-inducing agent, wherein polydeoxyadenine is added to at least one end of a sense strand and an antisense strand of the siRNA.

The above immunological tolerance-inducing agent, wherein at least one portion of the phosphodiester links of the polydeoxyadenine is phosphorothioated.

The above immunological tolerance-inducing agent, wherein the donor cell, tissue or organ is a cell derived from bone marrow.

The above immunological tolerance-inducing agent, wherein the costimulatory factor is that expressed in Dectin-1 expressing cell.

The above immunological tolerance-inducing agent, wherein the costimulatory factor is at least one member selected from the group consisting of CD40, B7.1 and B7.2.

The above immunological tolerance-inducing agent, wherein the costimulatory factor is CD40.

The above immunological tolerance-inducing agent, wherein the transplantation therapy is kidney transplantation, heart transplantation, lung transplantation, bone marrow transplantation, skin transplantation, or corneal transplantation.

A method for inducing immune tolerance in transplantation therapy, comprising a step of administering a nucleic acid-polysaccharide complex of an siRNA for a costimulatory factor and schizophyllan to an animal in need of immune tolerance for a donor cell, organ or tissue.

Use of a nucleic acid-polysaccharide complex of an siRNA for a costimulatory factor and schizophyllan for the manufacture of an immunological tolerance-inducing agent used for inducing donor-specific immune tolerance in a recipient in transplantation therapy of a donor cell, tissue or organ.

The immunological tolerance-inducing agent of the present invention can effectively induce donor-specific immune tolerance in a recipient receiving a donor cell, tissue or organ. More particularly, the present invention can introduce an siRNA for a costimulatory factor to a Dectin-1 expressing cell in a recipient treated or to be treated by transplantation therapy to induce RNAi activity, and therefore can regulate the function of the Dectin-1 expressing cell to induce immune tolerance in the recipient.

Furthermore, the use of the immunological tolerance-inducing agent of the present invention allows to provide a therapy in which immunosuppression can be induced by low dose of siRNA medicine. Especially, the use of the immunological tolerance-inducing agent of the present invention allows to inhibit rejection in transplantation therapy effectively.

DESCRIPTION OF EMBODIMENTS

Figure 1:
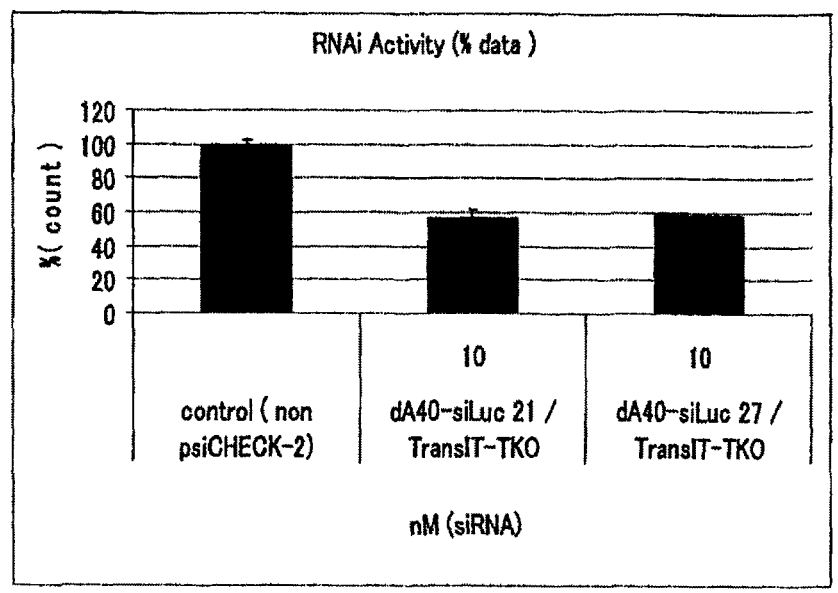
FIG. 1 is a chart showing the results of Example 4, or that is, an siRNA to which S-modified poly(dA) is linked can produce an RNA interference effect without being cleaved by Dicer.

The present invention is an immunological tolerance-inducing agent used for the induction of donor-specific immune tolerance in a recipient in transplantation therapy of a donor cell, tissue or organ, containing a nucleic acid-polysaccharide complex of an siRNA for a costimulatory factor and schizophyllan. Hereinafter, the immunological tolerance-inducing agent of the present invention will be described in detail.

siRNA for Costimulatory Factor

A target of siRNA used in the present invention may be a costimulatory factor (also referred to as costimulatory molecule), and is preferably a costimulatory factor which is expressed in Dectin-1 expressing cell. Dectin-1 is a receptor (pattern recognition receptor) that has a sugar chain recognition domain of a C-type leptin type present on the cell membrane. Dectin-1 extracellularly has a region that specifically recognizes β-1,3-glucan and intracellularly has a motif, called immunoreceptor tyrosinase-based activation motif-1 (ITAM), that delivers an activation signal. Once recognizing β-1,3-glucan, Dectin-1 facilitates production of NF-κB or an inflammatory cytokine to induce a biological defense response. In the present invention, examples of Dectin-1 expressing cells include macrophages, dendritic cells, neutrophils, and the like. It is known that schizophyllan has a β-1,3-glucan backbone, and is delivered into a Dectin-1 expressing cell through a signal induced when bound to Dectin-1 that is present on the cell membrane of a Dectin-1 expressing cell. The nucleic acid-polysaccharide complex used in the present invention is delivered into a Dectin-1 expressing cell because schizophyllan, which is a component of the complex, is recognized by Dectin-1. An siRNA contained in the nucleic acid-polysaccharide complex used in the present invention can efficiently induce immune tolerance in a recipient by selecting a costimulatory factor which is expressed in Dectin-1 expressing cell.

Specific examples of a costimulatory factor which is expressed in a Dectin-1 expressing cell include CD40, B7.1 (CD80), B7.2 (CD86) and the like. Examples of a target gene of siRNA used in the present invention include at least one of these genes, and a CD40 gene is particularly suitable.

A base sequence of "siRNA for a costimulatory factor" used in the present invention can be appropriately determined depending on types of a target costimulatory factor. An siRNA for a costimulatory factor may include a sequence that is 100% identical to a portion of the base sequence of the target costimulatory factor, or may include a sequence in which one or more bases are replaced and/or added relative to the 100% identical sequence as long as the desired RNA interference effect is obtained.

In a suitable example of the siRNA for costimulatory factor used in the present invention, the sense strand RNA and the antisense strand RNA are each composed of 21 ribonucleotides, with a dangling end composed of 2 ribonucleotides being formed at the 5' end of the sense strand RNA as well as the 5' end of the antisense strand RNA. That is, in the case of such a double strand RNA, the 1st to 19th ribonucleotides from the 3' end of the antisense strand RNA are complementary to the 3rd to 21st ribonucleotides from the 5' end of the sense strand RNA. Herein, such a 21 mer siRNA is also referred to as a 21 mer type siRNA. The 21 mer type siRNA is not cleavable by Dicer.

An siRNA for a costimulatory factor may be one that is capable of being complexed with schizophyllan, for example, one in which a molecule capable of being complexed with schizophyllan (hereinafter, also referred to as "SPG binding molecule") is added to at least one end of a sense strand or an antisense strand constituting an siRNA for a costimulatory factor gene.

The SPG binding molecule may be directly bound to the terminal ribonucleotide of the sense strand RNA and/or antisense strand RNA of the siRNA for a costimulatory factor or may be bound via a linker (spacer).

The number of SPG binding molecules which are added to the siRNA is not particularly limited.

One preferred example of siRNA to which a SPG binding molecule is added is one in which the number of binding of SPG binding molecule with an siRNA is one and the SPG binding molecule binds to the 5' end of sense strand of the siRNA. As just described, in the case where a SPG binding molecule binds only to the 5' end of sense strand of the siRNA, an RNA interference effect caused by the siRNA can be made significantly active.

Also, in the case of the 21 mer type siRNA, the SPG binding molecule may be bound to any of the sense strand/antisense strand and 5' end/3' end, and in the case where of the SPG binding molecule is bound to, in particular, the 5' end of the sense strand, a superior RNA interference effect can be demonstrated.

Types of the SPG binding molecule are not particularly limited as long as the molecule is complexed with schizophyllan, and are preferably nucleic acid, more preferably polydeoxyadenine (hereinafter, also referred to as "poly(dA)"). One poly(dA) chain and two schizophyllan chains can form a stable triple helix conformation.

In the case where poly(dA) is used as the SPG binding molecule, the number of deoxyadenines constituting the poly(dA) is not particularly limited as long as the complex formation with schizophyllan is possible, as described below, and it may be, for example, 10-100, preferably 20-100, more preferably 20-80, still more preferably 30-50.

In the case where poly(dA) is used as the SPG binding molecule, at least portion of phosphodiester link of the poly(dA) is desirably phosphorothioated (S modified). The proportion of S modified poly(dA) is generally 50% or more, preferably 80% or more, more preferably 100%. Herein, the proportion of S modified poly(dA) represents the proportion (%) of S modified phosphodiester links relative to total phosphodiester links of poly(dA). Also, the S-modified phosphodiester link shows a binding structure in which one oxygen atom of the phosphate residue of the phosphodiester link portion is replaced by a sulfur atom.

S modification on poly(dA) can be performed according to a known method. The distribution of S modification in the poly(dA) is not particularly limited, and the desired S modification may be performed on any location.

The S-modified poly(dA) forms a favorable complex with schizophyllan, and the nucleic acid-polysaccharide complex obtained in this manner has a high level of resistance to degrading enzymes. In the case where S modified poly(dA) is added to a sense strand in a 21 mer type siRNA, a nucleic acid-polysaccharide complex of the siRNA and schizophyllan is capable of making the RNA interference effect active by allowing an antisense strand to be incorporated into a RISC.

Schizophyllan

Schizophyllan (hereinafter, also referred to as "SPG") is a polysaccharide with a β-1,3-glucan backbone and is delivered into a cell through a signal that is induced when bound to Dectin-1, which is a receptor present on the surface of an antigen presenting cell.

SPG can be produced according to an ordinary method described in a document (A.C.S. 38(1), 253 (1997) or Carbohydrate Research, 89, 121-135 (1981)). Schizophyllan obtained in such a manner may be subjected to ultrasonication to give schizophyllan having a desired molecular weight.

A SPG used in the present invention may be one in which various functional molecules are bound together. In the case where a functional molecule is to be bound to SPG, the proportion of the functional molecule to be bound is, for example, 1 to 200, preferably 1 to 100, and particularly preferably 1 to 50 functional molecules relative to 100 side chains of SPG. The proportion of the functional molecule bound can be adjusted by controlling the amount of oxidizer added, such as sodium periodate, relative to the branched glucose residue in the aforementioned method. The binding site where the functional molecule binds to SPG and the binding site where the linker for the functional molecule is bound are not particularly limited, but it is preferable that the 1,2-diol portion of glucose with a 1,6-glucopyranoside link branched from the β-1,3-glucan backbone of SPG is substituted for binding.

The molecular weight of SPG used in the present invention is not particularly limited, and suitably set according to, for example, the chain length of the SPG binding molecule such as poly(dA). Specifically, the molecular weight of SPG is usually, for example, 25000 to 500000 and preferably 25000 to 250000.

Nucleic Acid-Polysaccharide Complex of siRNA for Costimulatory Factor and Schizophyllan In the immunological tolerance-inducing agent of the present invention, a nucleic acid-polysaccharide complex of an siRNA for a costimulatory factor and schizophyllan is used. The nucleic acid-polysaccharide complex can be obtained by allowing a SPG binding molecule which is added to an siRNA for a costimulatory factor to complex with schizophyllan.

Preferred examples of the nucleic acid-polysaccharide complex include a complex molecule in which poly(dA) that may be S modified is added to at least one end of a sense strand or an antisense strand constituting an siRNA for a costimulatory factor gene, and the one poly(dA) chain and two schizophyllan chains form a triple helix.

The nucleic acid-polysaccharide complex o can be prepared according to a known method. A specific example may be a production method that has the following steps (1) to (3): (1) the above-described siRNA to which a SPG binding molecule is bound directly or via a linker is prepared according to a known method, (2) separately, SPG is provided, or SPG (modified SPG) to which a functional molecule is bound directly or via a linker is prepared, and (3) a complex is then formed using the SPG binding molecule bound to the siRNA and the SPG or modified SPG.

In the step (3) of the method, the mixing ratio of the siRNA to the SPG or modified SPG can be suitably selected according to the chain length of the SPG binding molecule or the chain length of the SPG or modified SPG. In the case where the poly(dA) is used as the SPG binding molecule, one glucose molecule of the SPG backbone corresponds to one adenine molecule of the poly(dA), and one the poly(dA) chain and two SPG chains form a triple helix conformation. That is, in the nucleic acid-polysaccharide complex of the present invention, the poly(dA) is incorporated into one or more locations of the double helix conformation formed by two SPG chains, thus forming a triple helix conformation. For example, with an siRNA to which a 40 mer poly(dA) is added and SPG with a molecular weight of 150000, two molecules of SPG with a molecular weight 150000 and 17 molecules of an siRNA to which 40 mer poly(dA) is added form a triple helix conformation. A preferable molar ratio of the poly(dA)-added siRNA to SPG is 20:1 to 1:5, and preferably, they are mixed at 10:1 to 1:1, and the single strand polydeoxyadenine region of the polynucleotide-bound double strand RNA and the SPG or modified SPG are complexed. Subjecting the siRNA and the SPG or modified SPG to complex forming conditions in such a molar ratio enables these materials to efficiently interact with each other, thus making it possible to enhance the production efficiency of the nucleic acid-polysaccharide complex used in the present invention.

Specifically, a nucleic acid-polysaccharide complex forming a triple helix conformation using a poly(dA)-added siRNA and schizophyllan is prepared according to the following method. SPG adopts a triple helix conformation in a natural environment or in water. This SPG is dissolved in a polar solvent such as dimethylsulfoxide (DMSO) or an aqueous alkali solution such as an aqueous sodium hydroxide solution to be modified into single strands, then a poly(dA)-added siRNA is added, the solvent is replaced with water or the aqueous alkali solution is neutralized (regeneration process), and thereby a triple helical complex conformation (association structure) composed of one strand portion of poly(dA) linked with a siRNA and two strands of SPG is formed. It seems that such complex formation of a polynucleotide and a polysaccharide is mainly achieved through hydrogen bonding and a hydrophobic interaction.

Induction of Immune Tolerance

The immunological tolerance-inducing agent of the present invention is used for the induction of donor-specific immune tolerance in a recipient treated or to be treated by transplantation of a donor cell, tissue or organ. The use of the nucleic acid-polysaccharide complex allows to inhibit specifically expression of a costimulatory factor gene to Dectin-1 expressing cell and therefore, to induce donor-specific immune tolerance effectively.

The immunological tolerance-inducing agent of the present invention can be applied to animals such as humans, monkeys, mice, rats, dogs, rabbits, cats, bovines, and chickens, preferably humans.

The immunological tolerance-inducing agent of the present invention can be prepared by incorporating the nucleic acid-polysaccharide complex in an amount effective for the induction of immune tolerance and further combining a pharmaceutically acceptable carrier appropriately. Examples of such a carrier include aqueous carriers such as purified water, sugar-containing aqueous solutions, buffers, physiological saline, and nuclease-free water; excipients; and the like.

The administration route of the immunological tolerance-inducing agent can be suitably selected from methods conventionally used based on the patient's symptom, disease state, disease, and the like, such as oral, parenteral (including intravenous, intraperitoneal, intramuscular, subcutaneous, intrarectal, and intravaginal administration), inhalation, systemic administration, local administration (including external application to the skin or buccal cavity; infusion onto a site that does not substantially result in entry into the blood flow, such as the eye, ear, and nose).

The transplantation therapy using the immunological tolerance-inducing agent of the present invention is carried out by a method including the administration of the immunological tolerance-inducing agent of the present invention to a donor providing a cell, tissue or organ to be transplanted, a method including treatment of a cell, tissue or organ to be transplanted with the present immunological tolerance-inducing agent, a method including the administration to a recipient to be treated by transplantation of a cell, tissue or organ, or a method including the combination of two or three of these methods.

In transplantation therapy using the immunological tolerance-inducing agent of the present invention, a cell, organ or tissue to be transplanted is not particularly limited, and examples thereof include a cell derived from bone marrow, kidney, heart, lung, bone marrow, skin, cornea and the like.

The immunological tolerance-inducing agent of the present invention can treat or prevent resistance or rejection to a transplanted cell, organ or tissue as well as induce immune tolerance and therefore, can inhibit the occurrence of immunorejection even when the administration of the present immunosuppressor is discontinued at an early period after transplantation. Also, transplantation of a cell derived from donor bone marrow before living-donor liver transplantation or living-donor kidney transplantation, or administration of the immunological tolerance-inducing agent of the present invention when inducing immune tolerance in a recipient allows to promote the survival of the transplanted liver or kidney and avoid rejection thereof. The immunological tolerance-inducing agent of the present invention is also used in the treatment of autoimmune diseases, inflammatory diseases, proliferative and over-proliferative diseases, and cutaneous symptoms of immunologically mediated diseases (such as chronic rheumatoid arthritis, erythematodes, systemic erythematodes, Hashimoto's thyroiditis, multiple sclerosis, myasthenia gravis, type I diabetes, uveitis, nephrotic syndrome, psoriasis, atopic dermatitis, contact dermatitis, eczematous dermatitis, seborrheic dermatitis, lichen planus, pemphigus, bullous pemphigus, epidermolysis bullosa, hives, angioedema, angiitis, erythema, skin eosinophilia, and alopecia greata); and in the treatment of reversible obstructive airways diseases, gastroenteritis, allergies (such as inflammatory biliary disease, celiac disease, rectitis, eosinophilic gastroenteritis, mastocytosis, Crohn's disease, and ulcerative colitis), food-related allergies (such as migraine, rhinitis, and eczema), and other types of allergy.

In transplantation therapy, the dose of the immunological tolerance-inducing agent of the present invention may be an amount that is effective or non-toxic for the induction of immune tolerance, and the dose can be determined by those skilled in the art from routine experiments. The dose is not particularly limited, and for example, in the case where a complex of an siRNA for CD40 and a SPG is used as the nucleic acid-polysaccharide complex, the effective dose is generally selected from a range between about 0.001 and 10 mg per body weight (kg) per day.

The present invention also provides the use of the nucleic acid-polysaccharide complex for the preparation of an immunological tolerance-inducing agent used for the induction of donor-specific immune tolerance when a donor cell, tissue or organ is transplanted to a recipient. Additionally, the present invention provides a method for inducing immune tolerance including a step of administrating the nucleic acid-polysaccharide complex to an animal in need of immune tolerance for a donor cell, organ or tissue. Especially, the present invention also provides the use of the nucleic acid-polysaccharide complex for the preparation of a medicine for inhibition of rejection in transplantation therapy and induction of immune tolerance. Furthermore, the present invention provides a method for inhibiting rejection in transplantation therapy or a method for inducing immune tolerance, including a step of administrating the nucleic acid-polysaccharide complex to an animal in need of treatment or prevention of rejection for a transplanted organ or tissue.

The present application claims the propriety under PCT/JP2011/68265 filed on Aug. 10, 2011 and PCT/JP2012/53583 filed on Feb. 15, 2012, the entire contents of which are herein incorporated by reference.

EXAMPLES

The present invention shall be described in more detail below by way of examples, but the present invention is not limited thereto. Note that schizophyllan may be referred to as "SPG" in the examples. Also, the siRNA directed to luciferase may be referred to as "siLuc", and the siRNA directed to CD40 may be referred to as "siCD40".

Example 1

Formation of Nucleic Acid-Polysaccharide Complex of SPG and siRNA

The nucleic acid-polysaccharide complexes used in the following examples were formed as follows. SPG with a molecular weight of about 150000 was prepared so as to have a final concentration of 15 mg/ml in a 0.25 N aqueous sodium hydroxide solution, then stirred for 1 hour, and left to stand at 4° C. for 1 day for modification. A solution of an siRNA to which S-modified poly(dA) dissolved in 330 mM first sodium phosphate had been added was added to this modified SPG solution, and the mixture was neutralized and left to stand at 4° C. for no less than 24 hours. At this time, the mixture was prepared so as to have 0.27 mol of SPG per mol of siRNA. Note that, in the S-modified poly(dA)-added siRNA, 40 phosphorothioated deoxyadenines were linked with the 5' end of the sense strand of the siRNA by phosphoester links. In the following examples, the S-modified poly(dA) may be referred to as dA40(s). The extent of S modification of all the S-modified polydeoxyadenines used in the following examples was 100%.

Example 2

Stability of Nucleic Acid-Polysaccharide Complex of S-Modified Poly(dA)-Added siRNA and SPG in Cell Culture Medium Preparation was carried out so as to satisfy the conditions shown in Table 1 by adding a sample to a phosphate buffer (PBS) or a cell culture medium (10% FBS+RPMI) (FBS: Biological Industries Cat #04-001-1A, RPMI: Wako Pure Chemical Industries, Ltd., Cat #189-02025)). The sample was incubated at 37° C. for 4 hours or 24 hours, then subjected to electrophoresis under 100 V and 60 min conditions using 12.5% polyacrylamide gel (Tris-borate-EDTA (TBE)), and stained with SYBR Gold (Lifetechnologies Japan).

In Table 1, in dA40(s)-siLuc(21 nt), 40 mer phosphorothioated polydeoxyadenine was added to the 5' end of the sense strand of 21 mer siRNA (SEQ ID NO. 1) directed to luciferase. In dA40(s)-siLuc(27 nt), 40 mer phosphorothioated polydeoxyadenine was added to the 5' end of the sense strand of 27 mer siRNA (SEQ ID NO. 3) directed to luciferase.

TABLE 1

| Lane | Sample | Incubation |
|---|---|---|
| 1 | dA40(s)-siLuc(27 nt) | No incubation |
| 2 | dA40(s)-siLuc(27 nt) | 10% FBS + RPMI: 37° C., 24 hours |
| 3 | dA40(s)-siLuc(27 nt)/SPG complex | 10% FBS + RPMI: 37° C., 24 hours |
| 4 | dA40(s)-siLuc(21 nt) | No incubation |
| 5 | dA40(s)-siLuc(21 nt) | 10% FBS + RPMI: 37° C., 24 hours |
| 6 | dA40(s)-siLuc(21 nt)/SPG complex | 10% FBS + RPMI: 37° C., 24 hours |
| 7 | dA40(s)-siLuc(21 nt)/SPG complex | 10% FBS + RPMI: 37° C., 4 hours |
| 8 | dA40 | No incubation |
| 9 | 10% FBS + RPMI | No incubation |

As a result, with regard to the siRNAs to which 40 mer phosphorothioated poly(dA) had been added, samples that were not in the form of a complex of an siRNA and SPG in a degrading enzyme-containing cell culture medium (lanes 2 and 5) and the controls of lanes 1 and 4 had vague bands, indicating degradation, and samples that were in the form of a complex of an siRNA and SPG (lanes 3, 6, and 7) showed clearly visible bands, indicating that nucleic acid-polysaccharide complexes were stable. Note that samples with siRNAs to which phosphorothioated poly(dA) had been added were more stable in a degrading enzyme-containing cell culture medium than those with siRNAs to which non-phosphorothioated poly(dA) had been added.

Example 3

Dicer Sensitivity of Nucleic Acid-Polysaccharide Complex (3-1) Dicer Sensitivity of Nucleic Acid-Polysaccharide Complex with Non-5-Modified dA Tail In this example, a recombinant human dicer enzyme kit (manufactured by Genlantis Inc.: Cat #T510002) was used. Also, premixes having the following components (A to E) were prepared.

A. Nucleic acid sample: 2.5 μl (25 ng)
B. 10 mM ATP: 1 μl
C. 50 mM $MgCl_2$: 0.5 μl
D. Dicer reaction buffer: 4 μl
E. Recombinant Dicer enzyme (1 unit): 2 μl Samples B to D or B to E were mixed in a PCR tube, and then nucleic acid sample A was added. Then, nuclease-free distilled water was added such that the final volume was 10 μl. Then, incubation was carried out at 37° C. for 15 hours. After incubation, a stop solution was added to stop the reaction. Electrophoresis was carried out at 150 V for 80 min using 15% polyacrylamide gel (Tris-borate-EDTA (TBE)), and the gel was stained with SYBR (r) Gold (Lifetechnologies Japan).

In Table 2, siCD40(21 nt) denotes a 21 mer siRNA (SEQ ID NOs. 5 and 6) directed to CD40. In dA40-siCD40(21 nt), 40 mer polydeoxyadenine was added to the 5' end of the sense strand (SEQ ID NO. 5) of a 21 mer siRNA (SEQ ID NOs. 5 and 6) directed to CD40. siLuc21 denotes a 21 mer siRNA directed to luciferase shown in SEQ ID NOs 1 and 2. In dA40-siLuc(21 nt), 40 mer polydeoxyadenine was added to the 5' end of the sense strand (SEQ ID NO. 1) of a 21 mer siRNA (SEQ ID NOs. 1 and 2) directed to luciferase.

TABLE 2

| Lane | Sample |
|---|---|
| 1 | Marker |
| 2 | siCD40(21 nt) |
| 3 | dA40-siCD40(21 nt) |
| 4 | dA40-siCD40(21 nt): Dicer added |
| 5 | siLuc(21 nt) |
| 6 | dA40-siLuc(21 nt) |
| 7 | dA40-siLuc(21 nt): Dicer added |
| 8 | siLuc(27 nt) |
| 9 | dA40-siLuc(27 nt) |
| 10 | dA40-siLuc(27 nt): Dicer added |

Results of the above-described electrophoresis show that the electrophoresis band of lane 2 was as clearly visible as that of lane 3, and the band of lane 6 was as clearly visible as that of lane 7, and thus poly(dA)-siRNA(21 nt) is not cleavable by Dicer, but on the other hand, the band of lane 10 was more vague than that of lane 9, and poly(dA)-siRNA (27 nt) is cleavable by Dicer.

(3-2) Dicer Sensitivity of Nucleic Acid-Polysaccharide Complex with S-Modified dA Tail In the same manner as in (3-1) above, the Dicer sensitivity of a nucleic acid-polysaccharide complex with an S-modified dA tail was evaluated.

TABLE 3

| Lane | Sample |
|---|---|
| 1 | Marker |
| 2 | siLuc(21 nt) |
| 3 | siLuc(27 nt) |
| 4 | dA40(s)-siCD40(21 nt) |
| 5 | dA40(s)-siCD40(21 nt): Incubation with 37° C. warm water |
| 6 | dA40(s)-siCD40(21 nt): Dicer added |
| 7 | Marker |
| 8 | siLuc(21 nt) |
| 9 | siLuc(27 nt) |
| 10 | dA40(s)-siCD40(27 nt) |
| 11 | dA40(s)-siCD40(27 nt): Incubation with 37° C. warm water |
| 12 | dA40-siCD40(27 nt): Dicer added |

In Table 3, siLuc(21 nt) denotes a 21 mer siRNA (SEQ ID NOs. 1 and 2) directed to luciferase. siLuc(27 nt) denotes a 27 mer siRNA (SEQ ID NOs. 3 and 4) directed to luciferase. In dA40(s)-siCD40(21 nt), 40 mer phosphorothioated polydeoxyadenine was added to the 5' end of the sense strand (SEQ ID NO. 5) of a 21 mer siRNA (SEQ ID NOs. 5 and 6) directed to CD40. In dA40(s)-siCD40(27 nt), 40 mer phosphorothioated polydeoxyadenine was added to the 5' end of the sense strand (SEQ ID NO. 7) of a 27 mer siRNA (SEQ ID NOs. 7 and 8) directed to CD40.

Results of electrophoresis showed that the band of lane 6 was as clearly visible as those of lanes 4 and 5 and thus the 21 nt type siRNA, even when S-modified poly dA has been added thereto, is not cleavable by Dicer, but on the other hand, the band of lane 12 was vaguer than those of control lanes 10 and 11, and thus the 27 nt type siRNA is cleavable by Dicer.

Example 4

RNA Interference Effect of Poly(dA)-Linked siRNA

A Dual Luciferase expression vector psiCHECK™-2 (Promega Cat #C8021) was introduced into HEK 293 cells using Lipofectamine™ LTX (Lifetechnologies Japan, Cat #15338-500). At this time, the number of cells was adjusted so as to be 50000 per well. dA40-siLuc(21 nt) or dA40-siLuc(27 nt) was introduced into the cells using TransIT™-TKO (Takara Bio, Inc., Cat #V2154), and the cells were incubated at 37° C. for 20 hours in a $CO_2$ incubator. Then, a Dual Luciferase assay (manufactured by Promega, Dual-Glo Luciferase assay system, Cat #E2920) was carried out to measure the RNA interference effect. As a control, the same procedure was carried out without using a nucleic acid sample. With regard to the RNA interference effect, two luciferase expressions in the control were compared, and the RNA interference effect at that time was regarded as 0%, and the expression inhibition in each sample was expressed in %.

Results are shown in FIG. 1. It was shown that 21 mer dA40-siLuc(21 nt) linked with poly(dA), even without being cleaved by Dicer, yields the same RNA interference effect activity as 27 mer dA40-siLuc(27 nt).

Example 5

RNA Interference Effect of siRNA/SPG Complex Linked with S-Modified Poly(dA)

The RNA interference effect of a complex of SPG and a chimeric siRNA with phosphorothioated poly(dA) was evaluated using a Dual Luciferase assay (manufactured by Promega, Dual-Glo Luciferase assay system, Cat #E2920). RAW264.7 cells (dRAW cells), which strongly express Dectin-1, were used (obtained from associate professor Yoshiyuki Adachi (immunology) at Department of Pharmacology, Tokyo University of Pharmacy and Life Sciences). Samples used are shown in Table 4 below. In sample 4 in Table 3, dA40(s)-siLuc(21 nt) was introduced using a TransIT™-TKO (Takara Bio, Inc., Cat #V2154).

Results are also shown in Table 4 below.

TABLE 4

| | Sample | TransIT-TKO concentration (μl/ml) | siRNA concentration (nM) | RNA interference effect (%) |
|---|---|---|---|---|
| 1 | Control (psiCHECK ™-2 Co-Transfection) | — | 10 | 0 |
| 2 | siLuc(21 nt) | — | 10 | 8.8 |
| 3 | dA40(s)-siLuc(21 nt) | — | 10 | −4 |
| 4 | dA40(s)-siLuc(21 nt) (TransIT-TKO added) | 0.1 | 10 | 1.8 |
| 5 | dA40(s)-siLuc(21 nt)/SPG complex | — | 10 | 41 |

According to Table 4, it was shown that the poly(dA)(s)-siRNA/SPG complex yields an RNA interference effect.

Example 6

Dose Dependency of RNA Interference Effect by Poly(dA)(s)-siRNA Complex

In this example, the dose dependency of siRNA activity was checked. dRAW cells, which are proliferative in a 10% seroculture, were used. Samples used in this example are shown in Table 5 below.

This example was carried out according to the following procedure.

dRAW cells were recovered, seeded onto a 48-well plate so as to be 20000 cells/well/200 μl, incubated in a $CO_2$ incubator at 37° C. for 20 hours. A psiCHECK™-2/LTX complex in an amount of 20 μl/well and a culture medium in an amount of 180 μl/well were added to the 48-well plate. Then, a Dual Luc assay (manufactured by Promega, Dual-Glo Luciferase assay system, Cat #: E2920) was carried out. Results are shown in Table 5 below.

TABLE 5

| | Sample | siRNA concentration (nM) | RNA interference effect (%) |
|---|---|---|---|
| 1 | Control (Co-transfection) | 0 | 0 |
| 2 | Naked dA40(s)-siLuc(21 nt) | 100 | 14 |
| 3 | dA40(s)-siLuc(21 nt)/SPG complex | 1 | 12 |
| 4 | dA40(s)-siLuc(21 nt)/SPG complex | 10 | 21 |
| 5 | dA40(s)-siLuc(21 nt)/SPG complex | 100 | 36 |

From Table 5, it was shown that the poly(dA)(s)-siRNA complex yields an RNA interference effect in a dose dependent manner.

Example 7: Cell Introducibility of Poly(dA)(s)-siRNA Complex (7-A) Introducibility into dRAW Cells dRAW cells were seeded so as to be 1000000 cells/dish (5 ml) and incubated in a $CO_2$ incubator at 37° C. for 20 hours. Then, Alexa 647-labeled naked dA40(s)-siLuc(21 nt) and an Alexa 647-labeled dA40(s)-siLuc(21 nt)/SPG complex were added to culture media each in a concentration of 100 nM and brought into contact with dRAW cells. After each siRNA was added, cells were recovered 1, 2, 4, and 8 hours later. The recovered cells were fixed by 10% equilibrated formaldehyde (100 μl/dish), and the number of cells labeled with Alexia 647 was measured by flow cytometry (FACS).

According to the results, the number of cells labeled with Alexia 647 using the dA40(s)-siLuc(21 nt)/SPG was more than two times greater the number of labeled cells obtained using naked dA40(s)-siLuc(21 nt), and it seems that the cellular uptake of the dA40(s)-siLuc(21 nt)/SPG complex is more than two times greater.

(7-B) Introducibility into CD11c(+)

Spleen cells were obtained from mice (C57BL/6, male, 7 weeks old; 4 mice) in accordance with a standard method. Some of the obtained spleen cells were stored under refrigeration for use as a control. The remaining spleen cells were separated into a CD11c(−) cell group and a CD11c(+) cell group using a MACS MS column. Cell separation by the column was carried out twice. The CD11c(+) cell group was prepared so as to have $7 \times 10^5$ cells, and cultured on a 6-well plate (2 ml volume) for 48 hours (37° C., 5% $CO_2$) so as to satisfy the conditions shown in Table 6 below. After culturing, FACS analyses were carried out using the FACS antibodies shown in the parentheses in Table 6. In the table, Dectin-1-FITC denotes an anti-Dectin-1 antibody modified with FITC, CD11c-FITC denotes an anti-CD40 antibody modified with FITC, and PE Isotype control denotes an isotype control antibody modified with PE.

TABLE 6

| | Sample |
|---|---|
| 1 | CD11c(−) cells (Dectin-1-FITC) |
| 2 | CD11c(+) cells (PE Isotype control) |
| 3 | CD11c(+) cells (CD11c-FITC) |
| 4 | CD11c(+) cells (Dectin-1-FITC) |

TABLE 6-continued

| | Sample |
|---|---|
| 5 | CD11c(+) cells + SPG (Dectin-1-FITC) |
| 6 | CD11c(+) cells + 100 nM naked dA40(s)-siCD40(27 nt) (Dectin-1-FITC) |
| 7 | CD11c(+) cells + 100 nM dA40(s)-siCD40(27 nt)/SPG complex (Dectin-1-FITC) |

It was confirmed from the results that sample 5 has a smaller proportion of Dectin-1 positive cells than sample 4, sample 7 has a smaller proportion of Dectin-1 positive cells than samples 4 and 6, and when the siRNA/SPG complex is taken up into Dectin-1 expressing cells, the Dectin-1 expression level of the cells is decreased.

(7-C) Incorporation into RLC (RISC Loading Complex)

Spleen cells were obtained from mice (C57BL/6, male, 7 weeks old; 4 mice) in accordance with a standard method. Some of the obtained spleen cells were stored under refrigeration for use as a control. The remaining spleen cells were separated into a CD11c(−) cell group and a CD11c(+) cell group using a MACS MS column. Cell separation by the column was carried out twice. A CD11c(+) cell group was prepared so as to have $2 \times 10^4$ cells and cultured on a chamber cover glass (4 wells, 1 ml/well volume) for 24 hours (37° C., 5% $CO_2$). Then, siLuc in which the 5' end of the antisense strand had been labeled with Alexa 647 and a dA40(s)-siLuc/SPG complex in which the 5' end of the antisense strand had been labeled with Alexa 647 were added to CD11c(+) cells so as to achieve 100 nM, and the cells were cultured for 1 hour (37° C., 5% $CO_2$).

One hour later, the culture supernatant was removed by suction. 500 ml of a 4% paraformaldehyde/PBS solution was added to each well, and the cells were incubated for 15 minutes at room temperature. After removing the paraformaldehyde/PBS solution by suction, 1 ml of PBS was added to each well, the cells were incubated at room temperature for 5 minutes, and then PBS was removed by suction. This procedure was repeated once again (below, the procedure for 5 minute incubation at room temperature with PBS will be referred to as a washing procedure). 500 ml of a 0.1% Triton X-100/PBS solution was added to each well, the cells were incubated at room temperature for 10 minutes, and then the 0.1% Triton X-100/PBS solution was removed by suction. The washing procedure was carried out twice. 500 ml of a 10% normal goat serum (NGS)/PBS solution was added to each well, and the cells were incubated at room temperature for 30 minutes. After removing the 10% NGS/PBS solution by suction, an anti-TRBP2 mouse antibody was prepared so as to achieve 130 ng/ml with 0.1% Triton X-100, 1.5% NGS, and BSA/PBS, then 500 ml of the antibody was added to each well, and the cells were incubated at room temperature for 2 hours. The antibody solution was removed by suction, and the washing procedure was carried out 3 times. An Alexa 488 anti-mouse IgG antibody (Lifetechnologies Japan) was diluted 750-fold with Triton X-100, 1.5% NGS, and BSA/PBS, and the cells were incubated at room temperature for 1 hour. The antibody solution was removed by suction, and the washing procedure was carried out 3 times. After removing PBS by suction, the chamber was taken away, and a sample was mounted using a mounting medium containing an anti-fading agent. An image of this sample was taken with a laser confocal microscope and analyzed.

It was confirmed from the results that the siRNA of the dA40(s)-siLuc/SPG complex that had been taken up into the cells and TRBP2, which is the core protein of RLC, were localized in the same location, and images matched in the same focal depth. It is clear from the results that the siRNA taken up into the cells and TRBP2 are located within such a distance that they can interact with each other, or that is, the siRNA is incorporated in RLC. On the other hand, in the case where Alexa 647-labeled siLuc was used singly, no incorporated siLuc was observed.

(7-D) Inhibition of CD40 mRNA Expression In Vitro
(i) Real Time PCR

Passage-cultured dRAW cells (80% confluency) were suspended in a culture medium (10% FBS-RPMI (Lifetechnologies Japan, cat No. 12718011S)) and prepared so as to have $1 \times 10^5$ cells/ml. The cell suspension was added to a 96-well plate so as to have 10000 cells per well (100 μl/well) and cultured overnight under 37° C. and 5% $CO_2$ conditions. After culturing, the culture supernatant was removed by an aspirator, and 100 μl of a culture medium was added to each well. This procedure was repeated twice. The samples (Table 7) each adjusted so as to have a concentration of 100 nM using a culture medium in advance were added in an amount of 100 μl per well, and cultured for 20 hours under 37° C. and 5% $CO_2$ conditions. After culturing, 100 μl of a culture medium was added to each well, and the culture medium was then removed by an aspirator. 60 ng/ml of interferon-gamma (IFN-γ, PeproTech, cat No. 315-05) prepared using a culture medium in advance was added in an amount of 100 μl per well, and cultured for 4 hours under 37° C. and 5% $CO_2$ conditions. After culturing, total RNAs were prepared using a CellAmp Direct RNA Prep kit (Takara Bio, Inc., cat No. 37329) from the cells of each well. With the prepared total RNAs as templates, cDNAs were synthesized using a Primer Script RT reagent kit (Takara Bio, Inc., cat No. RR037A). The synthesized cDNAs were subjected to real time qPCR using SYBR Prime Ex Taq II (Takara Bio, Inc., cat No. RR081A) to measure CD40 mRNA expression levels. At the same time, the beta-actin mRNA expression levels were measured, and this was used to correct the measured CD40 mRNA values. The corrected values were regarded as the CD40 mRNA expression levels in respective conditions. The primer sequences used for qPCR are as shown in Table 8.

TABLE 7

| | Sample |
|---|---|
| 1 | No sample |
| 2 | dA40(s)-siCD40(21 nt)/SPG complex |
| 3 | SPG only |
| 4 | Naked dA40(s)-siCD40(21 nt) |

TABLE 8

| Mouse CD40 primer | Forward primer | CAAGGATTGCGAGGCATGTG | SEQ ID NO. 9 |
|---|---|---|---|
| | Reverse primer | TGACAGACGGTATCAGTGGT CTCAG | SEQ ID NO. 10 |
| Mouse β-actin primer | Forward primer | TGGCACCCAGCACAATGAA | SEQ ID NO. 11 |
| | Reverse primer | CTAAGTCATAGTCCGCCTA GAAGCA | SEQ ID NO. 12 |

It was confirmed from the results that the CD40 expression level achieved by the addition of only SPG or naked siCD40 to Dectin-1 expressing cells was not lower than that achieved by the control (no sample), or no RNAi activity was induced, but the addition of a siCD40/SPG complex to Dectin-1 expressing cells inhibited CD40 mRNA expression without weakening the original RNAi activity of the siRNA.
(ii) FACS CD11(+) cells in mouse spleen cells were separated, and the proportion of CD40 positive cells in the CD11(+) cells was analyzed by FACS. Moreover, the same environment as in cell culturing was used, or that is, cells were added to a 10% FBS+RPMI culture medium and cultured for specified 4 hours to 48 hours after being warmed to 37° C. in $CO_2$ incubation. At this time, the CD11(+) cells were treated with SPG, naked dA40(s)-siCD40(27 nt), and a dA40(s)-siCD40 (27 nt)/SPG complex, and the subsequent CD40 expression was analyzed by FACS. The method for treating the spleen cells is as described in (7-B) above. The antibodies used in FACS are shown in the parentheses in Table 9 below. In the table, PE Isotype control denotes an isotype control antibody modified with PE, and CD40-PE denotes an anti-CD40 antibody modified with PE.

TABLE 9

| | Sample |
|---|---|
| 1 | CD11c(+) cells (PE isotype control) |
| 2 | CD11c(+) cells (CD40-PE) |
| 3 | CD11c(+) cells + 100 nM naked dA40(s)-siCD40(27 nt) (CD40-PE) |
| 4 | CD11c(+) cells + 100 nM dA40(s)-siCD40(27 nt)/SPG complex (CD40-PE) |

Results showed that expressed CD positive cells are decreased with sample 4 and the siCD40/SPG complex inhibits CD40 expression on the primary cell surface. On the other hand, with siCD40 not in the form of a complex with SPG, no reduction in the number of CD40 positive cells was observed, and it was not possible to sufficiently inhibit CD40 expression.

It seems that in this example, a complex of an siRNA and SPG was formed, and thus the siRNA was stabilized in the serum and blood, thereby enabling the siRNA to be more efficiently introduced into cells than the naked siRNA and to be delivered into the cytoplasm, and as a result, mRNA expression was inhibited, and target molecule expression on the cellular membrane surface was inhibited.

Example 8

A costimulatory factor CD40, which is a known early response factor of an immunoreaction, was set as a target molecule, and cells of a responder mouse were treated with an siRNA directed to this molecule. The pharmacological effect was evaluated by carrying out a mixed lymphocyte reaction (MLR) between a stimulator cell group and an siRNA-treated or -untreated responder cell group and measuring the cell proliferation rates of the respective groups by a BrdU chemoluminescence kit.

Figure 2:
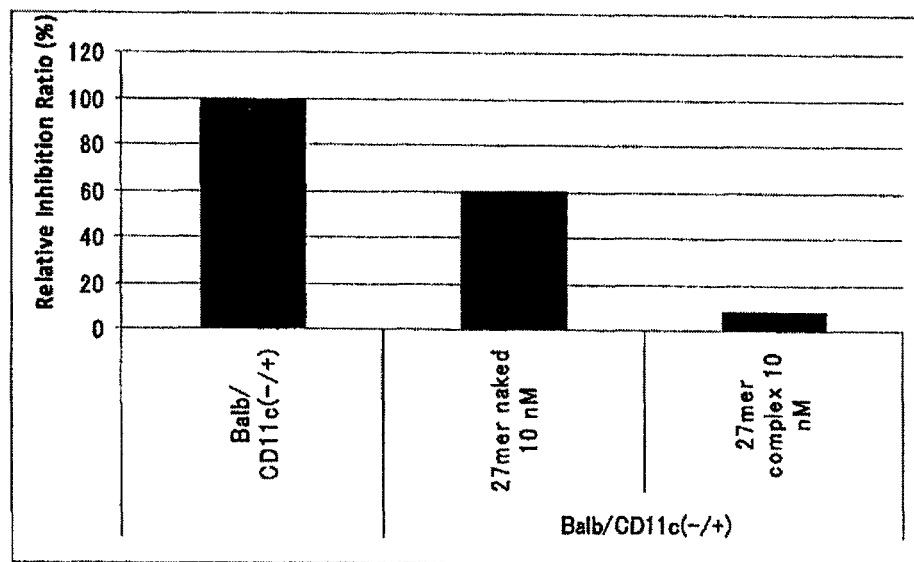
FIG. 2 is a chart showing the results of Example 8, i.e., inhibition of proliferation recovery by an alloreaction.
Figure 3:
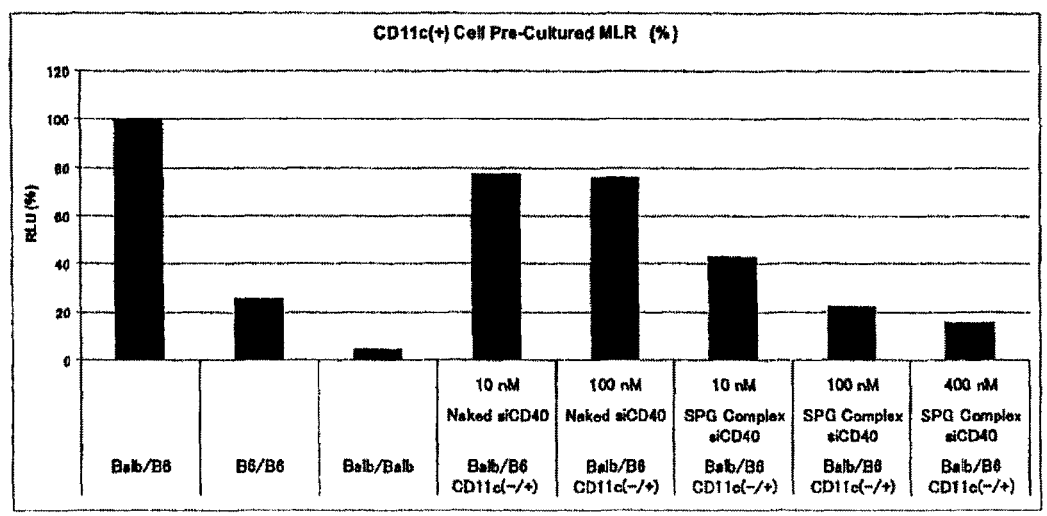
FIG. 3 is a chart showing the results of Example 8, or that is, CD11c positive cells with a dA40(s)-siCD40(27 nt)/SPG complex induce immunosuppression in preculture MLR.

When carrying out MLR, use of CD11c(−) responder spleen cells makes antigen presenting cells (APCs) deficient, thus suppressing a normal lymphocyte reaction and inhibiting cell proliferation. CD11c(+) spleen cells treated with an siCD40/SPG complex was added thereto, and the extent of cell proliferation recovery was observed. It was confirmed, from a comparison of allogeneic MLR and syngeneic MLR to which a dA40(s)-siCD40(27 nt)/SPG complex was added or not added, that notable induction of immunosuppression was achieved by adding the dA40(s)-siCD40(27 nt)/SPG complex (the extent of cell proliferation recovery was reduced: FIGS. 2 and 3).

In this example, a C57BL/6 mouse was used as a responder mouse, and Balb/c was used as a stimulator mouse. During MLR, the stimulator spleen cells were used after the cell proliferation of the stimulator spleen cells were stopped by mitomycin C (MMC) added when harvesting the stimulator spleen cells.

Pre-culture in vitro MLR refers to a method in which an siCD40/SPG complex is added to CD11c positive cells separated from the responder mouse spleen cells, then cells were brought back to a CD11 negative cell group and then mixed with mitomycin C (MMC)-treated stimulator spleen cells, and an MLR reaction is observed. That is, a dA40(s)-siRNA/SPG complex was bound (or introduced) to the target cells in advance, and immunosuppression induction in the MLR reaction was evaluated.

(8-A): Immunosuppressing Effect by Nucleic Acid-Polysaccharide Complex in Pre-Culture MLR Using CD11c Positive Cells In this test, whether the dA40(s)-siCD40(27 nt)/SPG complex demonstrates an immunosuppressing action or not was checked.

Cell Preparation

Spleen cells were collected from mice (Balb/c (9 weeks old male, 2 mice) and C57BL/6 (9 weeks old male, 2 mice)). Hemolyzing agents (ammonium chloride, potassium) were added to dissolve erythrocytes (5 ml hemolyzing agent, 5 ml RPMI). Cells were suspended in 10% FBS (DS Pharma Biomedical Co., Ltd.)+RPMI (5 ml), and the responder spleen cells were treated with mitomycin C (MMC) (25 μg MMC added to final $10^7$ cells).

Purification of CD11c Positive Cells (Magnetic Labeling)

Cells collected from the spleen cells were adjusted so as to have $10^8$ cells/sample and suspended in a buffer solution (400 μl). 100 μl of CD11c microbeads were added, and the cells were left to stand still in a refrigerator (2 to 8° C.) for 15 minutes.

Magnetic Separation

A column was rinsed with a buffer solution (MACS buffer: 2 mM EDTA, 0.5% BSA in PBS (1×) degassed after preparation), 500 μl of a suspension of magnetically labeled cells was poured with a pipette and allowed to flow out. The fluid that had flowed out was collected and used as CD11c (−) cells.

Procedure of Complex Group Addition

The collected CD11c positive cells were divided so as to be $1.0 \times 10^8$ cells/condition. Naked siCD40 and an siCD40/SPG complex were added thereto so as to have a final concentration of 100 nM, and the cells were incubated at 37° C. for 4 hours. $5 \times 10^8$ of responder cells (splenocytes) and $5 \times 10^8$ of stimulator cells (a mixture of $2.5 \times 10^4$ of CD11c positive cells and $4.75 \times 10^8$ of CD11c negative cells) were used in MLR. MLR conditions are shown in Table 10 below.

TABLE 10

MLR conditions

Sample

1 Allogeneic MLR Balbc/C57BL6 CD11c (−/+) control
2 Allogeneic MLR Balbc/C57BL6 CD11c (−/+) naked dA40(s)-siCD40 10 nM
3 Allogeneic MLR Balbc/C57BL6 CD11c (−/+) dA40(s)-siCD40/SPG complex 10 nM

* C57BL6 CD11c (−/+): The ratio of CD11c(−) cells and CD11c(+) cells mixed was CD11c(−): CD11c(+) = 95:5.
*In the table, unless specified otherwise, stimulator spleen cells were MMC-treated.
* In the table, MLR cells indicated as (Balbc/C57BL6) denote (mouse strain of lymphocytes used as stimulator/mouse strain of lymphocytes used as responder).
* In the table, siCD40 has base sequences shown in SEQ ID NOs. 7 and 8.

Results are shown in FIG. 2. FIG. 2 shows inhibition of proliferation recovery by an alloreaction. No cell proliferation was observed when all Balb/c spleen cells and CD11c (−) cells separated from C57BL/6 were subjected to MLR. On the other hand, when all Balb/c spleen cells and CD11c (−/+) cells separated from C57BL/6 were subjected to MLR, an allogeneic reaction was activated and a cell proliferation reaction was recovered. In the case where a complex was brought into contact with the target CD11c(+) cells, and then the cells were mixed back with CD11c(−) cells and subjected to MLR together with Balb spleen cells, cell proliferation recovery was inhibited. That is, it was shown that CD11c positive cells induce immunosuppression in pre-culture MLR.

(8-B): Dose Dependency of Immunosuppressive Action by Nucleic Acid-Polysaccharide Complex Using CD11c Positive Cells In this experiment, whether or not the dA40(s)-siCD40(27 nt)/SPG complex demonstrates an immunosuppressive action in a dose dependent manner was checked. Preparation of cells was carried out in the same manner as in (A) above using mice (Balb/c (7 week old males, 2 mice), C57BL/6 (7 week old males, 2 mice)). Also, purification and magnetic separation of CD11c positive cells were carried out in the same manner as in (A) above. MLR conditions are shown in Table 11 below.

TABLE 11

| | MLR conditions |
|---|---|
| | Sample |
| 1 | Allogeneic MLR (Balbc/C57BL6) |
| 2 | Syngeneic MLR (C57BL6/C57BL6) |
| 3 | Syngeneic MLR (Balbc/Balbc) |
| 4 | Allogeneic MLR (Balbc/C57BL6) CD11c (−/+) naked dA40(s)-siCD40(21 nt) 10 nM |
| 5 | Allogeneic MLR (Balbc/C57BL6) CD11c (−/+) naked dA40(s)-siCD40(21 nt) 100 nM |
| 6 | Allogeneic MLR (Balbc/C57BL6) CD11c (−/+) dA40(s)-siCD40(21 nt)/SPG complex 10 nM |
| 7 | Allogeneic MLR (Balbc/C57BL6) CD11c (−/+) dA40(s)-siCD40(21 nt)/SPG complex 100 nM |
| 8 | Allogeneic MLR (Balbc/C57BL6) CD11c (−/+) dA40(s)-siCD40(21 nt)/SPG complex 400 nM |

*In the table, unless specified otherwise, stimulator cells were MMC-treated.
* In the table, MLR cells are indicated as (mouse strain of lymphocytes used as stimulator/mouse strain of lymphocytes used as responder).

Results of MLR are shown in FIG. 3. FIG. 3 shows that CD11c positive cells induce immunosuppression in a dose dependent manner in pre-culture MLR.

Example 9

(9-A) In Vitro MLR

In this experiment, the lymphocyte growth inhibitory effect of the dA40(s)-siCD40(21 nt)/SPG complex administered in vitro was evaluated. The cell preparation method is as follows.

Spleen cells were collected from mice (stimulators: Balb/c (7 weeks old male, 2 mice) and responders: C57BL/6 (7 weeks old male, 2 mice)). Hemolyzing agents (ammonium chloride, potassium) were added to dissolve erythrocytes (3 ml hemolyzing agent, 2 min). 8 ml of RPMI was added, and the mixture was centrifuged at 300×g for 10 minutes. The supernatant was removed by an aspirator, and 10 ml of RPMI was added thereto to suspend the cells. Centrifugation and subsequent procedures were repeated. The supernatant was removed by an aspirator, then cells were suspended in 5 ml of 10% FBS/RPMI, and the cell count was measured. The spleen cells of the stimulator was treated with mitomycin C (MMC) (37° C., 30 min) (25 μg of MMC was added to the final $10^7$ cells). After MMC treatment, cells were suspended in 10 ml of RPMI and centrifuged at 300×g for 10 minutes. The supernatant was removed by an aspirator, 10 ml of RPMI was added thereto, and centrifugation and subsequent procedures were repeated 4 times. The supernatant was removed by an aspirator, then cells were suspended in 3 ml of 10% FBS/RPMI, the cell count was measured, and the cell concentration was adjusted so as to be $5 \times 10^6$ cells/ml. The complex (or siMOCK) was added to the spleen cells ($5 \times 10^6$ cells for each condition) of the responder so as to have a final concentration of 10 nM, and the cells were cultured for 4 hours at 37° C. After culturing, 10 ml of RPMI was added to the cell fluid to suspend the cells, and the cells were centrifuged at 300×g for 10 minutes. The supernatant was removed by an aspirator, 10 ml of RPMI was added thereto, and centrifugation and subsequent procedures were repeated 2 times. Cells were suspended in 1 ml of 10% FBS/RPMI, the cell count was measured, and the cell concentration was adjusted so as to be $5 \times 10^6$ cells/ml. $5 \times 10^5$ of the stimulator cells and $5 \times 10^5$ of the responder cells were mixed in one well (a final volume of 200 ml/well), and the cells were cultured in a 37° C. and 5% $CO_2$ environment for 72 hours. After culturing, cell growth was measured by an assay that uses chemoluminescence by BrdU uptake (Cell Proliferation ELISA, BrdU) (Roche Applied Science).

Also, in vitro MLR was carried out in which stimulator spleen cells were treated with an siRNA. The above-described procedure was carried out except that siRNA treatment was carried out after MMC treatment of stimulator cells and that responder cells after cell counting were stored under refrigeration without being treated until the beginning of MLR. MLR conditions are shown in Table 12.

TABLE 12

| Sample |
|---|
| MLR conditions (case where sample is added to responder spleen cells) |
| 1 Syngeneic MLR (C57BL6/C57BL6) |
| 2 Allogeneic MLR (Balbc/C57BL6) |
| 3 Allogeneic MLR (Balbc/C57BL6) dA40(s)-siCD40/SPG complex 10 nM |
| 4 Allogeneic MLR (Balbc/C57BL6) siMOCK (PBS) |
| MLR conditions (case where sample is added to stimulator spleen cells) |
| 1 Syngeneic MLR (C57BL6/C57BL6) |
| 2 Allogeneic MLR (Balbc/C57BL6) |
| 3 Allogeneic MLR (Balbc/C57BL6) dA40(s)-siCD40/SPG complex 10 nM |
| 4 Allogeneic MLR (Balbc/C57BL6) siMOCK (PBS) |
| 5 Allogeneic MLR (Balbc/C57BL6) SPG only (equivalent to 10 nM siRNA of complex) |
| 6 Allogeneic MLR (Balbc/C57BL6) naked dA40(s)-siCD40 10 nM |

It was confirmed from the results that in the MLR of responder cells treated with the dA40(s)-siCD40/SPG complex, the cell growth was about 60% of the cell growth with control siMock, and in the MLR of stimulator cells treated with the dA40(s)-siCD40/SPG complex, the cell growth was about 50% of the cell growth with control siMock. That is, it was confirmed that irrespective of the stimulator spleen cells or responder spleen cells, addition of the dA40(s)-siCD40/SPG complex inhibits the allogeneic MLR response to the syngeneic MLR response level. It is clear from these facts that the dA40(s)-siCD40/SPG complex significantly inhibits lymphocyte activation.

(9-B) Ex Vivo MRL

In this experiment, the behavior of siRNA in a living body was examined by administering a dA40(s)-siCD40(21 nt)/SPG complex into responder mice by a caudal vein injection (i.v.), collecting spleen cells after a lapse of 4 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the responder mice 4 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4 \times 10^5$ cells/wel), and the stimulator spleen cells were treated with mitomycin C (MMC) (25 μg MMC added to final $10^7$ cells). MLR conditions are shown in Table 14 below.

TABLE 13

| MLR conditions |
|---|
| Sample |
| 1 Medium |
| 2 Allogeneic MLR Balbc (MMC)/B6 (PBS) |
| 3 Allogeneic MLR Balbc (MMC)/B6 (20 μg SPG i.v.) |
| 4 Allogeneic MLR Balbc (MMC)/B6 (20 μg naked dA40(s)-siCD40(21 nt) i.v.) |
| 5 Allogeneic MLR Balbc (MMC)/B6 (20 μg dA40(s)-siCD40(21 nt)/SPG complex i.v.) |
| 6 Syngeneic MLR B6 (PBS i.v.)/B6 (PBS i.v.) |

Figure 4:
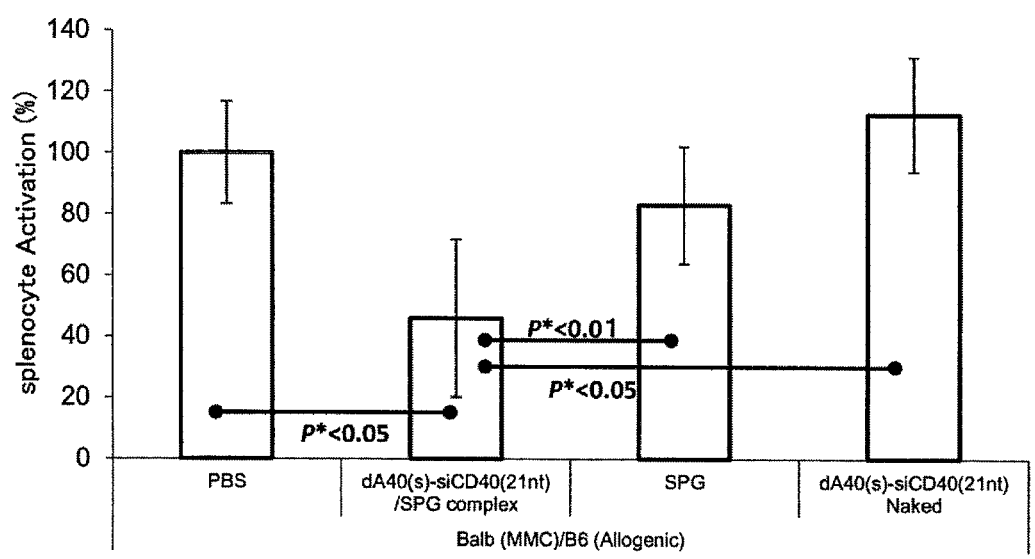
FIG. 4 is a chart showing the results of Example 9 (9-B), or that is, a dA40(s)-siCD40(21 nt)/SPG complex significantly inhibited activation of lymphocytes in ex vivo MLR.

Results are shown in FIG. 4. In FIG. 4, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It is clear from the results that the dA40(s)-siCD40(21 nt)/SPG complex significantly inhibits lymphocyte activation by administration into a living body.

Example 10: Cellular Uptake Specific to Dectin-1 Expression Cells

In this experiment, specific uptake of an Alexa 647-labeled dA40(s)-siLuc(21 nt)/SPG complex into Dectin-1 expressing cells was evaluated. The test method is as follows.

A 4-well chamber was coated with collagen Type I-P. Next, 500 μl of HEK 293 T cells and dHEK cells in a concentration of $1 \times 10^5$ cells/ml was added, and cultured overnight (37° C., 5% $CO_2$). Then, the culture medium was replaced to add a culture medium containing a 10 nM or 100 nM Alexa 647-labeled dA40(s)-siLuc(21 nt)/SPG complex, and cells were incubated for 2 to 8 hours at 37° C. in 5% $CO_2$. Next, cells were washed twice with PBS and fixed with 10% equilibrated formaldehyde. The fixed cells were observed under a laser confocal microscope (Carl Zeiss LSM710 NLO System), and the fluorescence intensity of Alexa 647 exhibited by the cells was measured by flow cytometry. Moreover, the level of Dectin-1 expressed on the surface of the fixed cells was measured by flow cytometry using an FITC-labeled antibody.

Note that the HEK 293 T cells used in this experiment are non-Dectin-1 expressing human embryonic kidney epithelial cells, and the dHEK cells are HEK 293 T cells that have been transformed so as to express Dectin-1.

Figure 5:
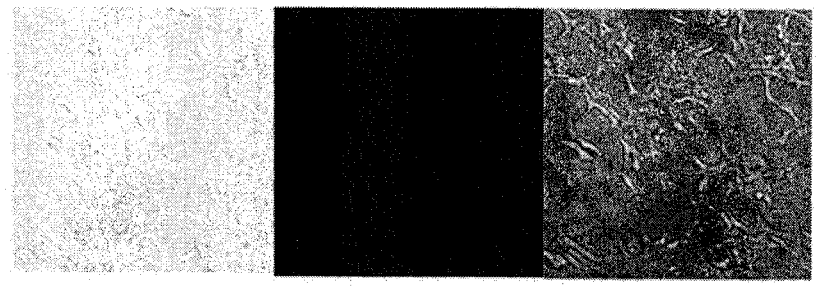
FIG. 5 shows images indicating the results of Example 10, i.e., HEK 293 T cells and dHEK cells treated with an Alexa 647-labeled dA40(s)-siLuc(21 nt)/SPG complex.
Figure 5:
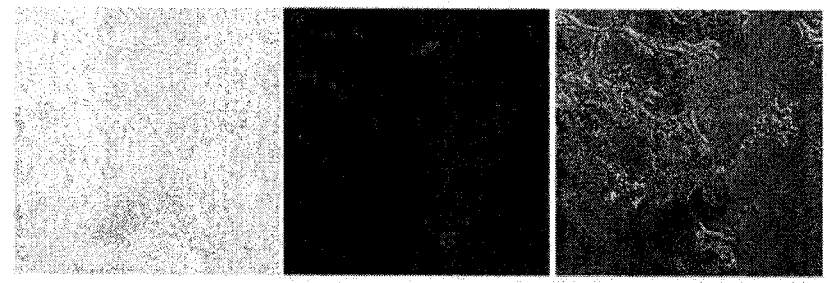
Figure 6:
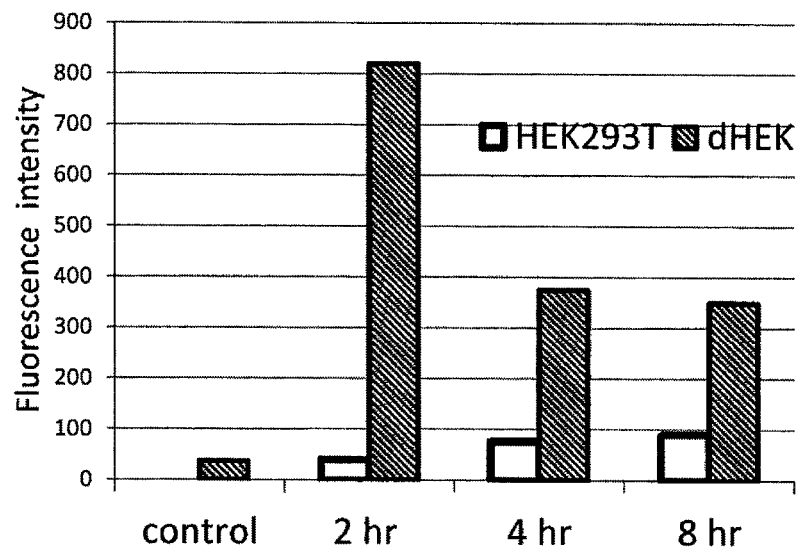
FIG. 6 shows the results of Example 10. That is, with regard to HEK 293 T cells and dHEK cells treated with an Alexa 647-labeled dA40(s)-siLuc(21 nt)/SPG complex, a chart showing the results of measuring the level of complex uptake (fluorescence intensity of Alexa 647) (FIG. 6A) and a chart showing the level of Dectin-1 expression on the cell surface (fluorescence intensity of FITC) (FIG. 6B).
Figure 6:
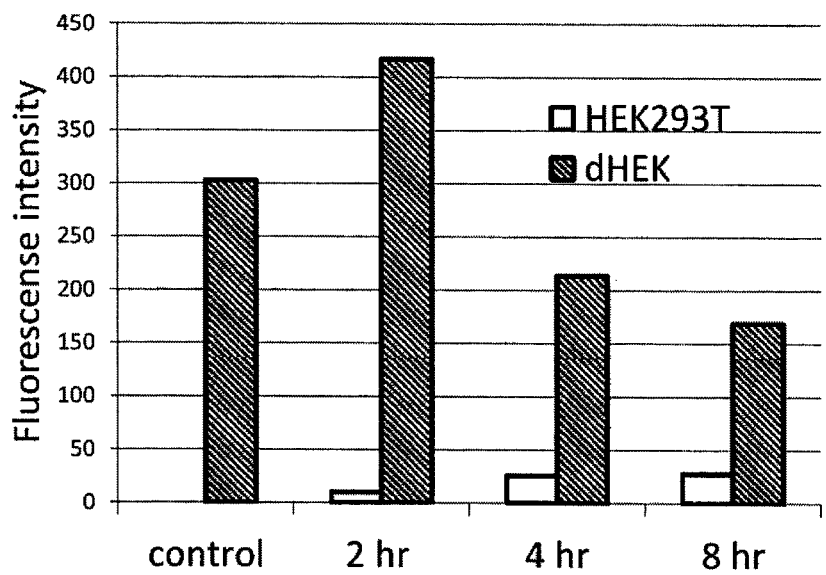

The obtained results are shown in FIGS. 5 and 6. FIG. 5 shows images of cells treated with the Alexa 647-labeled dA40(s)-siLuc(21 nt)/SPG complex, FIG. 6A shows the results of measuring the intensity of Alexa 647 fluorescence of the cells treated with the Alexa 647-labeled dA40(s)-siLuc(21 nt), and FIG. 6B shows the results of measuring the intensity of FITC fluorescence of the cells treated with the Alexa 647-labeled dA40(s)-siLuc(21 nt). It is clear from the results that the uptake of the Alexa 647-labeled dA40(s)-siLuc(21 nt)/SPG complex is confirmed only in Dectin-1-expressing dHEK cells, and the nucleic acid-polysaccharide complex of the present invention is taken up by endocytosis in Dectin-1 expression cells. Also, it is clear that the level of Dectin-1 expressed in dHEK cells decreases as the dA40(s)-siLuc(21 nt)/SPG complex is taken up, and thus Dectin-1 is taken up into the cells together with the dA40(s)-siLuc(21 nt)/SPG complex.

Example 11

(11-A)

In this experiment, the behavior of siRNA in a living body was examined by administering a dA40(s)-siCD40(21 nt)/SPG complex into responder mice by a caudal vein injection (i.v.), collecting spleen cells after a lapse of 4 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the responder mice 4 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4 \times 10^5$ cells/wel), and the stimulator spleen cells were treated with mitomycin C (MMC) (25 µg MMC added to final $10^7$ cells). MLR conditions are shown in Table 14.

TABLE 14

MLR conditions

| | Sample |
|---|---|
| 1 | Medium |
| 2 | Allogeneic MLR Balbc (MMC)/B6 (PBS) |
| 3 | Allogeneic MLR Balbc (MMC)/B6 (20 µg dA40(s)/SPG complex i.v.) |
| 4 | Allogeneic MLR Balbc (MMC)/B6 (20 µg dA40(s)-siCD40(21 nt)/SPG complex i.v.) |
| 5 | Allogeneic MLR Balbc (MMC)/B6 (20 µg dA40(s)-siLuc(21 nt)/SPG complex i.v.) |
| 6 | Syngeneic MLR B6 (PBS i.v.)/B6 (PBS i.v.) |

Figure 7:
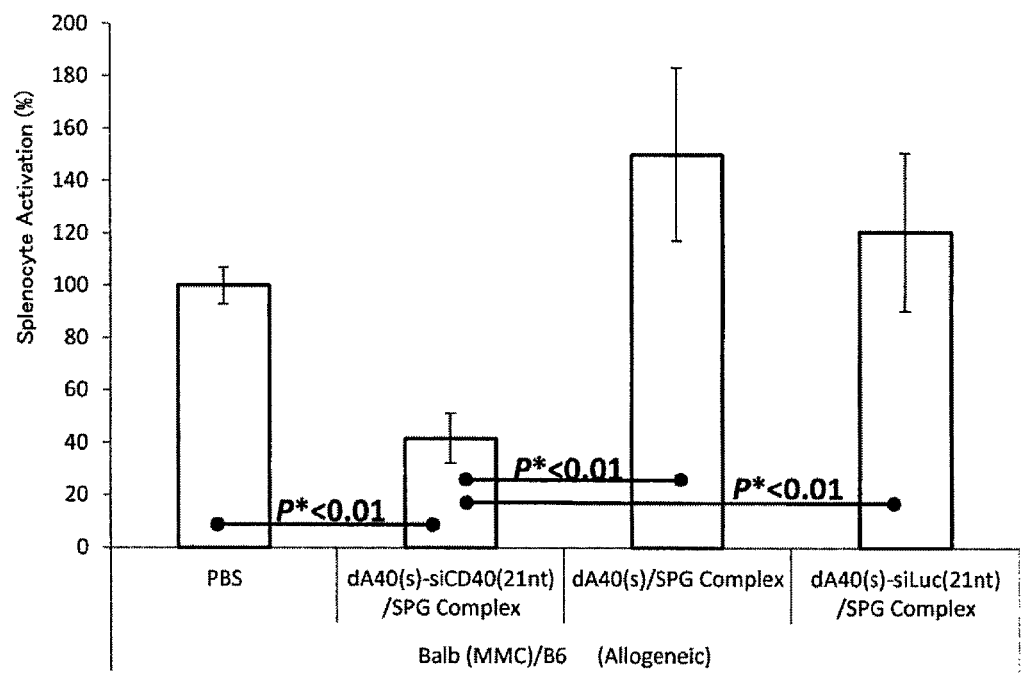
FIG. 7 is a chart showing the results of Example 11 (11-A), or that is, administration of a dA40(s)-siCD40(21 nt)/SPG complex significantly inhibited activation of lymphocytes.

The obtained results are shown in FIG. 7. In FIG. 7, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It is clear from the results that the dA40(s)-siCD40(21 nt)/SPG complex significantly inhibits lymphocyte activation by in vivo administration.

(11-B)

In this experiment, the behavior of siRNA in a living body was examined by administering a dA40(s)-siCD40(21 nt)/SPG complex into both responder mice and stimulator mice by a caudal vein injection (i.v.), collecting spleen cells after a lapse of 12 hours, and carrying out MLR with stimulator mouse spleen cells. The cell preparation method is as follows.

Spleen cells were collected from mice (stimulators: Balb/c (8 weeks old male, 3 mice) and responders: C57BL/6 (8 weeks old male, 3 mice)). An siRNA/SPG complex was intravenously injected into the stimulator mice and the responder mice 12 hours before collecting spleen cells. Hemolyzing agents (ammonium chloride, potassium) were added to dissolve erythrocytes (5 ml hemolyzing agent, 5 ml RPMI). Cells were suspended in 5 ml of 10% FBS (DS Pharma Biomedical Co., Ltd.)+RPMI ($4 \times 10^5$ cells/wel), and the stimulator spleen cells were treated with mitomycin C (MMC) (25 µg MMC added to final $10^7$ cells). MLR conditions are shown in Table 15.

TABLE 15

MLR conditions

| | Sample |
|---|---|
| 1 | Medium |
| 2 | Allogeneic MLR Balbc (MMC)/B6 (PBS) |
| 3 | Allogeneic MLR Balbc (MMC)/B6 (20 µg dA40(s)-siLuc(21 nt)/SPG complex i.v.) |
| 4 | Allogeneic MLR Balbc (MMC)/B6 (20 µg dA40(s)-siCD40(21 nt) and SPG separately present in solution i.v.) |
| 5 | Allogeneic MLR Balbc (MMC)/B6 (20 µg dA40(s)-siCD40(21 nt)/SPG complex i.v.) |
| 6 | Syngeneic MLR B6 (PBS i.v.)/B6 (PBS i.v.) |

Figure 8:
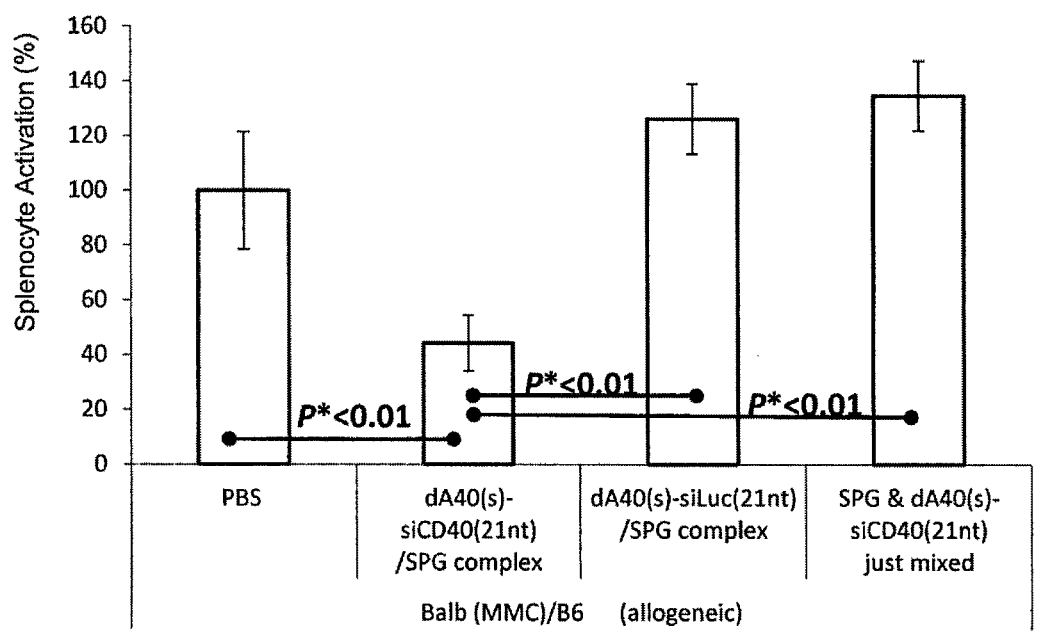
FIG. 8 is a chart showing the results of Example 11 (11-B), or that is, administration of a dA40(s)-siCD40(21 nt)/SPG complex significantly inhibited activation of lymphocytes.

The obtained results are shown in FIG. 8. In FIG. 8, the value (splenocyte activity) obtained by subtracting the numerical value of the syngeneic reaction from the numerical value of the allogeneic reaction of a control (value obtained by subtracting the sample 2 cell count from the sample 6 cell count) is plotted as 100%, and how much the lymphocyte proliferative reaction resulting from the allogeneic reaction was inhibited by the administration of the dA40(s)-siCD40(21 nt)/SPG complex is shown. It was confirmed also from the results that, as with the results of (9-A) above, the dA40(s)-siCD40(21 nt)/SPG complex significantly inhibits lymphocyte activation by in vivo administration.

Example 12

Spleen cells were collected from Balb/c mice. Cells were seeded onto a 24-well plate in an amount of $5 \times 10^6$ cells/well, and an RPMI culture medium containing 10 vol % FBS was added so as to achieve 1 ml/well. A dA40(s)-siCD40(21 nt)/SPG complex (300 ng/well in terms of siRNA) that used SPG with side chain modification by biotin or a PBS-containing control sample as siMock was added to the plate, and cultured in a $CO_2$ incubator (37° C.) overnight. The culture medium was removed by suction, then cells were resuspended in 10 mM Tris-HCl (PH 7.5) containing 100 mM NaCl and 1 mM EDTA and disrupted for 15 seconds by a sonicator, 50 ml of streptavidin-labeled magnetic particles (Roche Applied Science, cat No. 11641778001) were added, and a reaction was carried out at room temperature for 15 minutes while stirring. Centrifugation was carried out to collect a precipitate, the resulting precipitate was resuspended in 100 µl of a sodium dodecyl sulfate (SDS) buffer, subjected to SDS-polyacrylamide electrophoresis, and transferred to a nitrocellulose membrane. Next, detection of TRBP2 was carried out with a mouse anti-TRBP2 antibody and a peroxidase-bound anti-mouse IgG antibody.

As a result, it was found that dA40(s)-siCD40(21 nt) that is in the form of a complex with SPG is in a complex form with TRBP2.

Example 13

The effect of a dA40(s)-siCD40(21 nt)/SPG complex was studied in cardiac allograft by using model mice of heterotopic cardiac transplantation.

More specifically, a dA40(s)-siCD40(21 nt)/SPG complex was administered through the tail vein to donor mice (C57/BL10, male) and recipient mice (CBA, male) at a dose of 2 µg/head. The dosage schedules are as follows. A dose of 2 µg/head at one time was administered to the donor mouse 3 days before (on day −3) and 1 day before (on day −1) cardiac extirpation, and a dose of 2 mg/head at one time was administered to the recipient mouse 3 days before (on day −3) and 1 day before (on day −1) transplantation in the same way. On day 0, the heart was excised from the donor mouse, and the heart was surgically transplanted heterotopically into the recipient mouse. After the transplantation, each dose of 2 µg/head of a dA40(s)-siCD40(21 nt)/SPG complex at one time was further administered through the tail vein to the recipient mouse 1 day (day 1), 3 days (day 3), 5 days (day 5), and 7 days (day 7) after the cardiac transplantation. After the completion of administration, the heartbeat of the transplanted heart of the recipient mouse was observed over time. In addition, as a comparison, a test where a dA40(s)-siGAPDH(glyceraldehyde-3-phosphate dehydrogenase)(21 nt)/SPG complex instead of the dA40(s)-siCD40(21 nt)/SPG complex was administered in the same amount and a test where the dA40(s)-siCD40(21 nt)/SPG complex was not administered were performed in the same manner as above.

Figure 9:
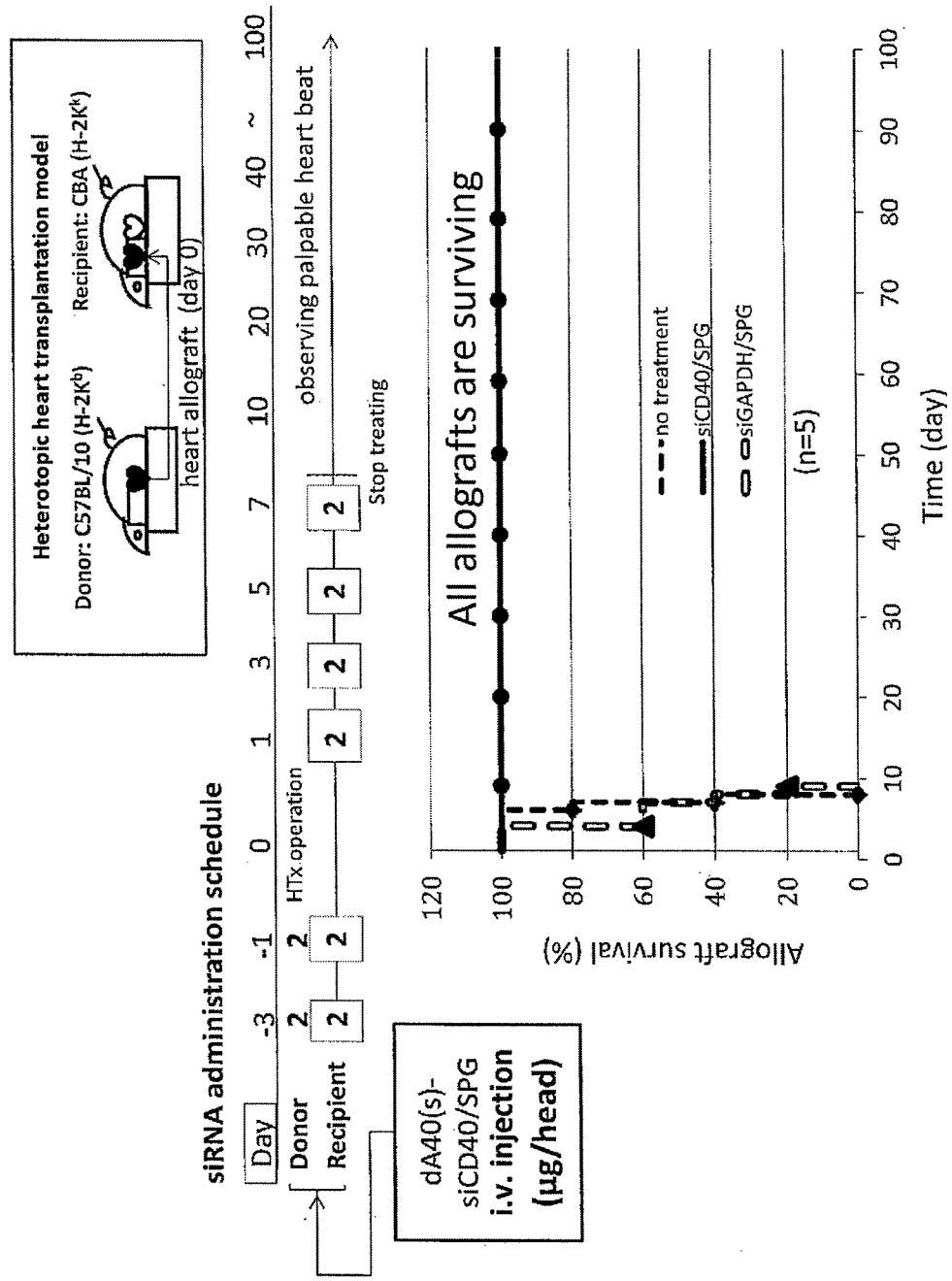
FIG. 9 is a chart showing the results of Example 13, or that is, in a mouse model of heterotopic cardiac transplantation administered with a dA40(s)-siCD40(21 nt)/SPG complex, the heartbeat of the transplanted heart is normal for a long period of time and the survival rate after transplantation is high.

The obtained results are shown in FIG. 9. In FIG. 9, "siCD40/SPG complex" indicates a dA40(s)-siCD40(21 nt)/SPG complex, and "siGAPDH/SPG complex" indicates a dA40(s)-siGAPDH(21 nt)/SPG complex. As can be seen from FIG. 9, when the dA40(s)-siCD40(21 nt)/SPG complex was administered, the beat of the transplanted heart was normal for a long period of time in all the recipient mice after the transplantation, and survival of all recipient mice was confirmed even at 90 days after the transplantation. On the other hand, when the dA40(s)-siGAPDH(21 nt)/SPG complex was administered or nothing was administered, the survival rate of the recipient mice was 0% on day 10 after the transplantation.

Moreover, when the dA40(s)-siCD40(21 nt)/SPG complex was administered to only donor mice (C57/BL10, male) at a dose of 2 µg/head, or administered to only recipient mice (CBA, male) at a dose of 2 µg/head, the beat of the transplanted heart was observed. As a result, the beat of the transplanted heart was observed over a long period of time even in the case where only donor mice or only recipient mice received the administration.

From these results, it is believed that the dA40(s)-siCD40 (21 nt) was effectively introduced into antigen-presenting cells to suppress the expression of CD40 so that the activation of antigen-specific T cells was suppressed.

Example 14

Ectopic cardiac transplantation model mice were used and an immune tolerance effect of a dA40(s)-siCD40(21 nt)/SPG complex by adoptive transfer was examined.

Specifically, 2 µg/head of a dA40(s)-siCD40(21 nt)/SPG complex was administered to a first Donor mouse (C57BL/10, male) and a first Recipient mouse (CBA/N, male) via tail veins. The administration regime is as follows. To the first Donor mouse, the dA40(s)-siCD40(21 nt)/SPG complex was administered at 2 µg/head per dose 3 days (day −3) and 1 day (day −1) before the isolation of heart, and to the first Recipient mouse, the dA40(s)-siCD40(21 nt)/SPG complex was administered at 2 mg/head per dose 3 days (day −3) and 1 day (day −1) before transplantation in the same manner as described above. On day 0, the heart was isolated from the first Donor mouse and the isolated heart was surgically transplanted at ectopic site in the first Recipient mouse. After transplantation, to the first Recipient mouse, the dA40(s)-siCD40(21 nt)/SPG complex was administered via tail vein at 2 µg/head per dose 1 day (day 1), 3 days (day 3), 5 days (day 5), and 7 days (day 7) after cardiac transplantation. At end of the administration, in the first Recipient mouse, beats of the transplanted heart were observed over time. Then, spleen cells were isolated from the first Recipient mouse at the time when the days that the transplanted heart was beating reached 30 days, and to a second Recipient mouse (CBA/N, male) receiving $5 \times 10^7$ cells via tail vein, the isolated spleen cells were administered, followed by isolating heart from a second Donor mouse (C57BL/10, male), and the isolated heart was surgically transplanted at ectopic site in the second Recipient mouse (30 Day A.T. (B10 to CBA) group). At end of ectopic cardiac transplantation, beats of the transplanted heart in the second Recipient mouse were observed over time.

As comparative groups, each group in the case where ectopic cardiac transplantation was carried out under the same conditions as the above-described conditions except that Balb/c (male) was used as a first Recipient mouse (30 Day A.T. (Balb/c to CBA) group); in the case where ectopic cardiac transplantation was carried out under the same conditions as the above-described conditions except that spleen cells were isolated from the first Recipient mouse at the time when the days that the transplanted heart of the first Recipient mouse was beating reached 100 days (100 Day A.T. (B10 to CBA) group); and in the case where ectopic cardiac transplantation was carried out under the same conditions as the above-described conditions except that the dA40(s)-siCD40(21 nt)/SPG complex was not administrated to the first Recipient mouse and the first Donor mouse (Naive A.T. (B10 to CBA) group) was examined in the same manner as described above.

Figure 10:
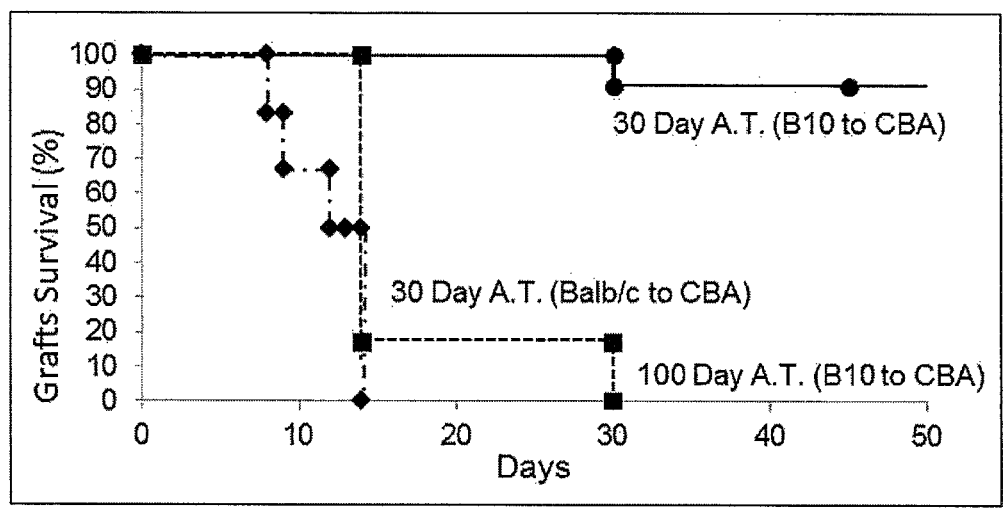
FIG. 10 shows the results of Example 14 that estimated an immune tolerance effect of a dA40(s)-siCD40(21 nt)/SPG complex by adoptive transfer in ectopic cardiac transplantation model mice.

The obtained results are shown in FIG. 10. As indicated clearly in FIG. 10, in the case where a dA40(s)-siCD40(21 nt)/SPG complex was administered, the percentage that the transplanted heart of the second Recipient mouse was normally beating over a long period was dramatically high, so that the second Recipient mouse kept the survival rate of 90% even at 50 days after transplantation. On the other hand, in the 30 Day A.T. (Balb/c to CBA) group, 100 Day A.T. (B10 to CBA) group and Naive A.T. (B10 to CBA) group, the transplanted heart of the second Recipient mouse was not normally beating at 20 days after transplantation, so that the second recipient mouse had the survival rate of 0% at 30 days after transplantation in all these groups.

It is clear from the results that a dA40(s)-siCD40(21 nt)/SPG complex has a high ability of inducing donor-specific immune tolerance.

Example 15

An immune tolerance effect of a dA40(s)-siCD40(21 nt)/SPG complex was examined by MLR. Specifically, MLR was carried out according to the following method.

Preparation of Recipient (Responder) Cells

Spleen cells were collected from a mouse (CBA, male) and T cells were sorted from the collected cells using a T-Cell Enrichment (nylon fiber) column to prepare Recipient cells.

Preparation of Donor (Stimulator) Cells

Bone marrow-derived dendritic cells (BMDC) were collected from a mouse (C57BL/10, male), and the collected cells were exposed to 20 Gy of radiation to prepare stimulator cells.

ectopic site in the Recipient mouse. After transplantation, to the Recipient mouse, the dA40(s)-siCD40(21 nt)/SPG complex was administrated via tail vein at 2 µg/head per dose 1 day (day 1), 3 days (day 3), days (day 5), and 7 days (day 7) after cardiac transplantation. At end of the administration, in the Recipient mouse, beats of the transplanted heart were observed over time. Then, spleen cells were collected from the Recipient mouse at the time when the days that the transplanted heart was beating reached 30 days. Each of CD4(+)CD25(−) T cells, CD11c(−) T cells (macrophage), CD4(+)CD25(+) T cells (Treg, regulatory T cell) and CD11c (+) dendritic cells derived from CBA treated by ectopic cardiac transplantation was sorted from the collected spleen cells by a cell sorter to prepare Regulator cells.

Meanwhile, the spleen cells were collected from a mouse (CBA, male) not receiving a dA40(s)-siCD40(21 nt)/SPG complex and not treated by ectopic cardiac transplantation. Subsequently, CD11c(+) dendritic cells derived from Naive CBA were separated from the obtained spleen cells to prepare Stimulator cells.

MLR Conditions

Stimulator cells, regulator cells and responder cells were mixed in a well containing 10% FBS/RPMI and the mixture were cultured at 37° C. under 5% $CO_2$ environment. After culturing, proliferation of responder cells was measured by an assay that uses chemoluminescence by BrdU uptake (Cell Proliferation ELISA, BrdU) (Roche Applied Science). MLR conditions are shown in Table 16.

TABLE 16

| | Responder cells | Stimulator cells | Regulator cells |
|---|---|---|---|
| Condition 1 | T cells derived from CBA | | |
| Condition 2 | T cells derived from CBA | BMDC derived from C57BL/10 | |
| Condition 3 | T cells derived from CBA | CD11c(+) dendritic cells derived from CBA | |
| Condition 4 | T cells derived from CBA | BMDC derived from C57BL/10 | CD4(+)CD25(−) T cells derived from CBA treated by ectopic cardiac transplantation |
| Condition 5 | T cells derived from CBA | BMDC derived from C57BL/10 | CD11c(−) T cells derived from CBA treated by ectopic cardiac transplantation |
| Condition 6 | T cells derived from CBA | BMDC derived from C57BL/10 | CD4(+)CD25(+) T cells derived from CBA treated by ectopic cardiac transplantation |
| Condition 7 | T cells derived from CBA | BMDC derived from C57BL/10 | CD11c(+) dendritic cells derived from Naive CBA |
| Condition 8 | T cells derived from CBA | BMDC derived from C57BL/10 | CD11c(+) dendritic cells derived from CBA treated by ectopic cardiac transplantation |

Meanwhile, the spleen cells were collected from a mouse (CBA, male) and then CD11c(+) dendritic cells were separated from the obtained spleen cells to prepare stimulator cells.

Preparation of Regulator Cells

Figure 11:
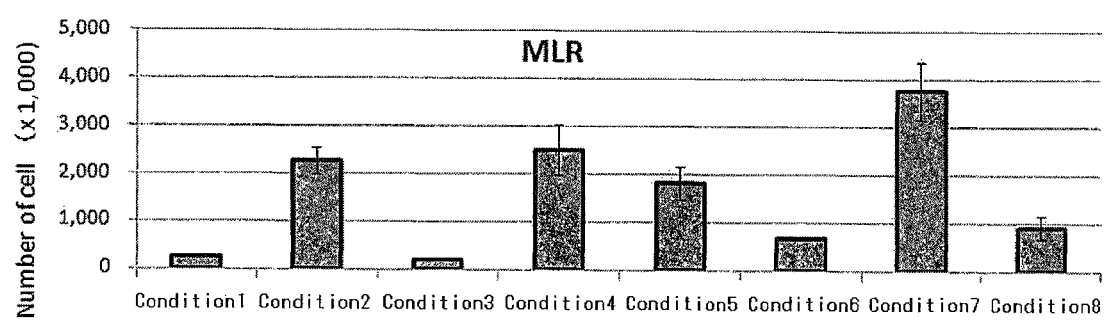
FIG. 11 shows the results of Example 15 that estimated an immune tolerance effect of a dA40(s)-siCD40(21 nt)/SPG complex by MLR.

To a Donor mouse (C57BL/10, male) and a Recipient mouse (CBA, male), 2 µg/head of a dA40(s)-siCD40(21 nt)/SPG complex was administrated via tail veins. The administration regime is as follows. To the Donor mouse, the dA40(s)-siCD40(21 nt)/SPG complex was administrated at 2 µg/head per dose 3 days (day −3) and 1 day (day −1) before the isolation of heart, and to the Recipient mouse, the dA40(s)-siCD40(21 nt)/SPG complex was administrated at 2 mg/head per dose 3 days (day −3) and 1 day (day −1) before transplantation in the same manner as described above. On day 0, the heart was isolated from the Donor mouse and the isolated heart was surgically transplanted at The obtained results are shown in FIG. 11. It is found from the results that in the case where CD11c(+) dendritic cells derived from Naive CBA were used as Regulator cells, Recipient cells were greatly increased. On the contrary, in the case where T cells and dendritic cells derived from CBA receiving a dA40(s)-siCD40(21 nt)/SPG complex and treated by ectopic cardiac transplantation were used as Regulator cells, the increase of Recipient cells was inhibited. Especially, in the case where CD4(+)CD25(+) T cells and CD11c(+) dendritic cells derived from CBA treated by ectopic cardiac transplantation were used, the increase of Recipient cells was significantly inhibited.

It is indicated from the results of MLR that the dA40(s)-siCD40(21 nt)/SPG complex has a high donor-specific immune tolerance effect.

Note that the nucleotide sequences of siLuc and siCD40 used in Examples 1 to 15 are as shown in Table 17 below.

TABLE 17

| siLuc (21 nt) sequence (5'→3') | Sense | GGC CUU UCA CUA CUC CUA CGA | SEQ ID NO. 1 |
|---|---|---|---|
| | Antisense | GUA GGA GUA GUG AAA GGC CAG | SEQ ID NO. 2 |
| siLuc (27 nt) sequence (5'→3') | Sense | CUG GCC UUU CAC UAC UCC UAC GAG CAC | SEQ ID NO. 3 |
| | Antisense | GUG CUC GUA GGA GUA GUG AAA GGC CAG | SEQ ID NO. 4 |

TABLE 17-continued

| siCD40 (21 nt) sequence (5'→3') | Sense | GGA GGG CAC CGC AGA AUC AUU | SEQ ID NO. 5 |
|---|---|---|---|
| | Antisense | UGA UUC UGC GGU GCC CUC CUU | SEQ ID NO. 6 |
| siCD40 (27 nt) sequence (5'→3') | Sense | AAG GAG GGC ACC GCA GAA UCA GAC ACU | SEQ ID NO. 7 |
| | Antisense | AGU GUC UGA UUC UGC GGU GCC CUC CUU | SEQ ID NO. 8 |

The invention claimed is:

1. A method for inducing immune tolerance in transplantation therapy, comprising a step of intravenously administering a nucleic acid-polysaccharide complex, the complex consisting of an siRNA which inhibits CD40 gene expression, to which polydeoxyadenine is added, and schizophyllan to an animal in need of immune tolerance for a donor cell, organ or tissue.

2. The method according to claim 1, wherein in the immunological tolerance-inducing agent, polydeoxyadenine is added to at least one end of a sense strand and an antisense strand of the siRNA.

3. The method according to claim 2, wherein in the immunological tolerance-inducing agent, at least one portion of the phosphodiester links of the polydeoxyadenine is phosphorothioated.

4. The method according to claim 1, wherein the donor cell, tissue or organ is a cell derived from bone marrow.

5. The method according to claim 1, wherein the transplantation therapy is kidney transplantation, heart transplantation, lung transplantation, bone marrow transplantation, skin transplantation, or corneal transplantation.

* * * * *

```
                        SEQUENCE LISTING

<160> NUMBER OF SEQ ID NOS: 12

<210> SEQ ID NO 1
<211> LENGTH: 21
<212> TYPE: RNA
<213> ORGANISM: Artificial
<220> FEATURE:
<223> OTHER INFORMATION: Sense strand of siLuc(21nt)

<400> SEQUENCE: 1
ggccuuucac uacccuacg a                                              21

<210> SEQ ID NO 2
<211> LENGTH: 21
<212> TYPE: RNA
<213> ORGANISM: Artificial
<220> FEATURE:
<223> OTHER INFORMATION: Antisense strand of siLuc(21nt)

<400> SEQUENCE: 2
guaggaguag ugaaaggcca g                                             21

<210> SEQ ID NO 3
<211> LENGTH: 27
<212> TYPE: RNA
<213> ORGANISM: Artificial
<220> FEATURE:
<223> OTHER INFORMATION: Sense strand of siLuc(27nt)

<400> SEQUENCE: 3
cuggccuuuc acuacuccua cgagcac                                       27

<210> SEQ ID NO 4
<211> LENGTH: 27
<212> TYPE: RNA
<213> ORGANISM: Artificial
<220> FEATURE:
<223> OTHER INFORMATION: Antisense strand of siLuc(27nt)

<400> SEQUENCE: 4
gugcucguag gaguagugaa aggccag                                       27

<210> SEQ ID NO 5
<211> LENGTH: 21
<212> TYPE: RNA
<213> ORGANISM: Artificial
<220> FEATURE:
<223> OTHER INFORMATION: Sense strand of siCD40(21nt)

<400> SEQUENCE: 5
ggagggcacc gcagaaucau u                                             21

<210> SEQ ID NO 6
```

```
<211> LENGTH: 21
<212> TYPE: RNA
<213> ORGANISM: Artificial
<220> FEATURE:
<223> OTHER INFORMATION: Antisense strand of siCD40(21nt)

<400> SEQUENCE: 6
ugauucugcg gugcccuccu u                                             21

<210> SEQ ID NO 7
<211> LENGTH: 27
<212> TYPE: RNA
<213> ORGANISM: Artificial
<220> FEATURE:
<223> OTHER INFORMATION: Sense strand of siCD40(27nt)

<400> SEQUENCE: 7
aaggagggca ccgcagaauc agacacu                                       27

<210> SEQ ID NO 8
<211> LENGTH: 27
<212> TYPE: RNA
<213> ORGANISM: Artificial
<220> FEATURE:
<223> OTHER INFORMATION: Antisense strand of siCD40(27nt)

<400> SEQUENCE: 8
agugucugau ucugcggugc ccuccuu                                       27

<210> SEQ ID NO 9
<211> LENGTH: 20
<212> TYPE: DNA
<213> ORGANISM: Artificial
<220> FEATURE:
<223> OTHER INFORMATION: Forward primer for mouse CD40

<400> SEQUENCE: 9
caaggattgc gaggcatgtg                                               20

<210> SEQ ID NO 10
<211> LENGTH: 25
<212> TYPE: DNA
<213> ORGANISM: Artificial
<220> FEATURE:
<223> OTHER INFORMATION: Reverse primer for mouse CD40

<400> SEQUENCE: 10
tgacagacgg tatcagtggt ctcag                                         25

<210> SEQ ID NO 11
<211> LENGTH: 19
<212> TYPE: DNA
<213> ORGANISM: Artificial
<220> FEATURE:
<223> OTHER INFORMATION: Forward primer for mouse beta-actin

<400> SEQUENCE: 11
tggcacccag cacaatgaa                                                19

<210> SEQ ID NO 12
<211> LENGTH: 25
<212> TYPE: DNA
<213> ORGANISM: Artificial
```

```
<220> FEATURE:
<223> OTHER INFORMATION: Reverse primer for mouse be-ta-actin

<400> SEQUENCE: 12
ctaagtcata gtccgcctag aagca                                          25
```